US008034338B2

(12) United States Patent
Loibner et al.

(10) Patent No.: US 8,034,338 B2
(45) Date of Patent: Oct. 11, 2011

(54) IMMUNOGENIC RECOMBINANT ANTIBODY

(75) Inventors: Hans Loibner, Vienna (AT); Gottfried Himmler, Vienna (AT); Günter Waxenecker, Mank (AT); Manfred Schuster, Schrick (AT); Thomas Putz, Innsbruck (AT)

(73) Assignee: Igeneon Krebs-Immuntherapie Forschungs-Und Entwicklungs-AG, Vienna (AU)

( * ) Notice: Subject to any disclaimer, the term of this patent is extended or adjusted under 35 U.S.C. 154(b) by 241 days.

(21) Appl. No.: 10/552,324

(22) PCT Filed: Apr. 16, 2004

(86) PCT No.: PCT/EP2004/004059
§ 371 (c)(1),
(2), (4) Date: Oct. 7, 2005

(87) PCT Pub. No.: WO2004/091655
PCT Pub. Date: Oct. 28, 2004

(65) Prior Publication Data
US 2007/0258978 A1 Nov. 8, 2007

(30) Foreign Application Priority Data

Apr. 17, 2003 (AT) .................................. A 599/2003

(51) Int. Cl.
A61P 39/00 (2006.01)
C07K 16/42 (2006.01)
C12N 15/63 (2006.01)
C12P 21/08 (2006.01)
A61K 39/395 (2006.01)
C12N 1/00 (2006.01)

(52) U.S. Cl. .................... 424/131.1; 435/69.6; 436/547; 530/387.2; 530/387.3

(58) Field of Classification Search ................ 424/131.1; 435/69.5; 436/547; 530/387.2, 387.3
See application file for complete search history.

(56) References Cited

U.S. PATENT DOCUMENTS 5,977,315 A 11/1999 Chatterjee et al.
2005/0163768 A1* 7/2005 Eckert et al. ............... 424/131.1

FOREIGN PATENT DOCUMENTS

| CA | 2360382 | 7/2000 |
| CA | 2391927 | 5/2001 |
| DE | 10059930 | 5/2002 |
| EP | 0285059 | 10/1988 |
| EP | 0759442 | 2/1997 |
| WO | WO-9324647 | 12/1993 |
| WO | 97/40140 A1 | 10/1997 |
| WO | WO-0041722 | 7/2000 |
| WO | 01/21796 A2 | 3/2001 |
| WO | WO-0135989 | 5/2001 |
| WO | WO 03/074679 * | 9/2003 |
| WO | WO-03097663 | 11/2003 |

OTHER PUBLICATIONS

Campbell et al, Biology, 5th ed. p. 856, 1999.*
Fundamental Immunology 242 (William E. Paul, M.D. ed., 3d ed. 1993).*
MacCallum et al. (J. Mol. Biol. (1996) 262:732-745).*
Pascalis et al. The Journal of Immunology (2002) 169, 3076-3084.*
Casset et al. (2003) BBRC 307, 198-205.*
Vajdos et al. (2002) J. Mol. Biol. 320, 415-428.*
Holm et al (2007) Mol. Immunol. 44: 1075-1084.*
Chen et al. J. Mol. Bio. (1999) 293, 865-881.*
Wu et al. J. Mol. Biol. (1999) 294, 151-162.*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
ATCC search output for HB 9347 hybridoma.*
ATCC search output for HB 9324 hybridoma.*
Wright et al (Springer Semin Immunopathology ,15 :259-273 (1993)).*
Delente (Trends in Biotechnology 3, letters to editor, No. 9, (1985)).*
Olden et al (Biochem et Biophys Acta 650:209-232 (1982)).*
Salfeld (Nature Biotech. 25(12): 1369-1372 (2007)).*
Lund et al. (The Journal of Immunology 1996, 157:4963-4969).*
ATCC website search output for "HB-9324" (p. 1, Feb. 2, 2009).*
ATCC website search output for "HB-9347" (p. 1, Feb. 2, 2009).*
Debe et al. (U.S. Appl. No. 09/791,537, filed Feb. 2, 2001).*
Sequence search alignment for SEQ ID No. 3 (p. 1, Sep. 12, 2009).*
Steinitz, M. et al., "Human monoclonal anti-idiotypic antibodies. I. Establishment of immortalized cell lines from a tumor patient treated with mouse monoclonal antibodies", Journal of Immunology, Nov. 15, 1988, vol. 141, No. 10, pp. 3516-3522.
Fagerberg, J. et al., "Humoral anti-idiotypic and anti-anti-idiotypic immune response in cancer patients treated with monoclonal antibody 17-1A", Cancer Immunology, Immunotherapy: CII, 1996, vol. 42, No. 2, pp. 81-87 (Abstract).
Brumeanu, T.-D. et al., "Engineering of doubly antigenized immunoglobulins expressing T and B viral epitopes," Immunotechnology, 1996, vol. 2, pp. 85-95.
Saleh, M. et al., "Generation of a human anti-idiotypic antibody that mimics the GD2 antigen" Journal of Immunology, vol. 151, No. 6, Sep. 15, 1993, pp. 3390-3398.
Waxenecker, G. et al., "Qualitative and quantitative dissection of the immune response to the cancer vaccine candidates IGN101 and IGN301" Proceedings of the Annual Meeting of the American Association for Cancer Research, vol. 43, Mar. 2002, pp. 560.
Wallick, C.S. et al., "Glycosylation of a VH residue of a monoclonal antibody against alpha (1-6) dextran increases its affinity for antigen" Journal of Experimental Medicine, vol. 168, Sep. 1988, pp. 1099-1109.

* cited by examiner

Primary Examiner — Lynn Bristol
(74) Attorney, Agent, or Firm — Birch, Stewart, Kolasch & Birch, LLP

(57) ABSTRACT

The invention refers to an immunogenic recombinant antibody designed for immunization of primates comprising at least a part of a murine IgG2a subtype amino acid sequence and a mammalian glycosylation.

6 Claims, 9 Drawing Sheets

Figure 1:
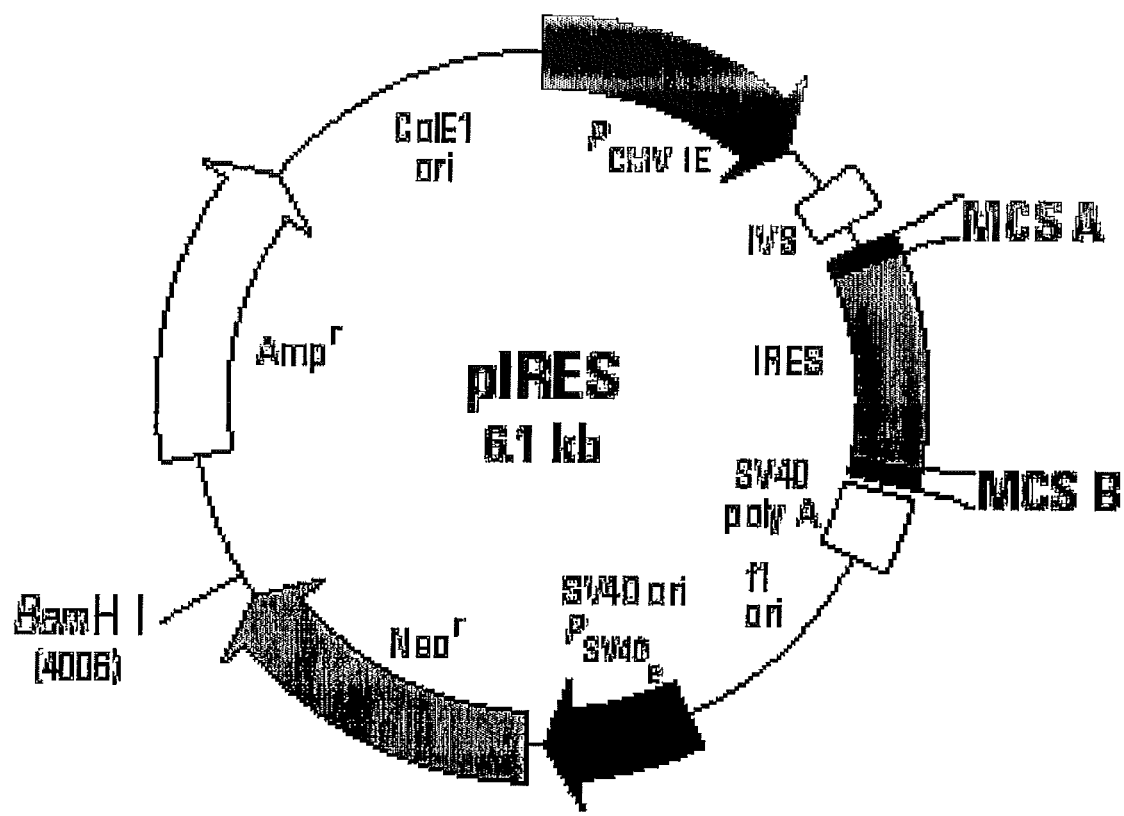

```
                    Xho I       KOZAK
5'...ATA GGC TAG C CTC GAG CCA CCA CCA TG CAT CAG ACC AGG ATG GG
CATCAAGATGGAATCACAGACTCTGGTCTTCATATCCATACTGCTCTGGTTATATG
GAGCTGATGGGAACATTGTAATGACCCAATCTCCCAAATCCATGTCCATGTCAGTA
GGAGAGAGGGTCACCTTGACCTGCAAGGCCAGTGAGAATGTGGTTACTTATGTTT
CNTGGTATCAACAGAAACCAGAGCAGTCTCCTAAACTGCTGATATATGGGGCATC
CAACCGGTACACTGGGGTCCCNGATCGCTTCACAGGCAGTGGATCTGCAACAGA
TTTCACTCTGACCATCAGCAGTGTGCAGGCTGAAGACCTTGCAGATTATCACTGT
GGACAGGGTTACAGCTATCCGTACACGTTCGGAGGGGGGACCAAGCTGGAAATA
AAACGGGCTGATGCTGCACCAACTGTATCCATCTTCCCACCATCCAGTGAGCAGT
TAACATCTGGAGGTGCCTCAGTCGTGTGCTTCTTGAACAACTTCTACCCCAAAGA
CATCAATGTCAAGTGGAAGATTGATGGCAGTGAACGACAAAATGGCGTCCTGAAC
AGTTGGACTGATCAGGACAGCAAAGACAGCACCTACAGCATGAGCAGCACCCTCA
CCTTGACCAAGGACGAGTATGAACGACATAACAGCTATACCTGTGAGGCCACTCA
CAAGACATCAACTTCACCCATTGTCAAGA
                    Mlu I   Bam HI
GC TTC AAC AGG AAT GAG TGT TAG ACG CGT GGA TCC GCC CCT CTC CCT
CCCCCCCCCTAACGTTACTGGCCGAAGCCGCTTGGAATAAGGCCGGTGTGCGT
TTGTCTATATGTGATTTTCCACCATATTGCCGTCTTTTGGCAATGTGAGGGCCCGG
AAACCTGGCCCTGTCTTCTTGACGAGCATTCCTAGGGGTCTTTCCCCTCTCGCCA
AAGGAATGCAAGGTCTGTTGAATGTCGTGAAGGAAGCAGTTCCTCTGGAAGCTTC
TTGAAGACAAACAACGTCTGTAGCGACCCTTTGCAGGCAGCGGAACCCCCCACCT
GGCGACAGGTGCCTCTGCGGCCAAAAGCCACGTGTATAAGATACACCTGCAAAG
GCGGCACAACCCCAGTGCCACGTTGTGAGTTGGATAGTTGTGGAAAGAGTCAAAT
GGCTCTCCTCAAGCGTATTCAACAAGGGGCTGAAGGATGCCCAGAAGGTACCCC
```

FIG 3A

ATTGTATGGGATCTGATCTGGGGCCTCGGTGCACATGCTTTACATGTGTTTAGTC
GAGGTTAAAAAAACGTCTAGGCCCCCCGAACCACGGGGACGT

KOZAK Nco I

G GTT TTC CTT TGA AAA ACA CGA TCA TAA TAT GCC CAC CAC CAT GG
AATGGAGCAGAGTCTTTATCTTTCTCCTATCAGTAACTGCAGGTGTTCACTCCAG
GTCCAGTTGCAGCAGTCTGGAGCTGAGCTGGTAAGGCCTGGGACTTCAGTGAAG
GTGTCCTGCAAGGCTTCTGGATACGCCTTCACTAATTACTTGATAGAGTGGGTAAA
GCAGAGGCCTGGACAGGGCCTTGAGTGGATTGGGGTGATTAATCCTGGAAGTGG
TGGTACTAACTACAATGAGAAGTTCAAGGGCAAGGCAACACTGACTGCAGACAAA
TCCTCCAGCACTGCCTACATGCAGCTCAGCAGCCTGACATCTGATGACTCTGCGG
TCTATTTCTGTGCAAGAGATGGTCCCTGGTTTGCTTACTGGGGCCAAGGGACTCT
GGTCACTGTCTCTGCAGCCAAAACAACAGCCCCATCGGTCTATCCACTGGCCCCT
GTGTGTGGAGATACAACTGGCTCCTCGGTGACTCTAGGATGCCTGGTCAAGGGTT
ATTTCCCTGAGCCAGTGACCTTGACCTGGAACTCTGGATCCCTGTCCAGTGGTGT
GCACACCTTCCCAGCTGTCCTGCAGTCTGACCTCTACACCCTCAGCAGCTCAGTG
ACTGTAACCTCGAGCACCTGGCCCAGCCAGTCCATCACCTGCAATGTGGCCCAC
CCGGCAAGCAGCACCAAGGTGGACAAGAAAATTGAGCCCAGAGGGCCCACAATC
AAGCCCTGTCCTCCATGCAAATGCCCAGCACCTAACCTCTTGGGTGGACCATCCG
TCTTCATCTTCCCTCCAAAGATCAAGGATGTACTCATGATCTCCCTGAGCCCCATA
GTCACATGTGTGGTGGTGGATGTGAGCGAGGATGACCCAGATGTCCAGATCAGC
TGGTTTGTGAACAACGTGGAAGTACACACAGCTCAGACACAAACCCATAGAGAGG
ATTACAACAGTACTCTCCGGGTGGTCAGTGCCCTCCCCATCCAGCACCAGGACTG
GATGAGTGGCAAGGAGTTCAAATGCAAGGTCAACAACAAAGACCTCCCAGCGCC
CATCGAGAGAACCATCTCAAAACCCAAAGGGTCAGTAAGAGCTCCACAGGTATAT
GTCTTGCCTCCACCAGAAGAAGAGATGACTAAGAAACAGGTCACTCTGACCTGCA
TGGTCACAGACTTCATGCCTGAAGACATTTACGTGGAGTGGACCAACAACGGGAA
AACAGAGCTAAACTACAAGAACACTGAACCAGTCCTGGACTCTGATGGTTCTTACT

FIG 3B

TCATGTACAGCAAGCTGAGAGTGGAAAAGAAGAACTGGGTGGAAAGAAATAGCTA
CTCCTGTTCAGTGGTCCACCAGGGTCTGCACAATCACCACACGACTAAGAGCTTC
TC

*Sal I*

C CGG ACT CCG GGT AAA TGA GTC GAC
ACGCGTCGAGCATGCATCTAGGGCGGCCAATTCCGCCCCTCTCCGTCCCCCCC
CCTAACGTTACTGGCCGAAGCCGCTTGGAATAAGGCCGGTGTGCGTTTGTCTATA
TGTGATTTTCCACCATATTGCCGTCTTTTGGCAATGTGAGGGCCCGGAAACCTGG
CCCTGTCTTCTTGACGAGCATCCTAGGGGTCTTTCCCCTCTCGCCAAAGGAATG
CAAGGTCTGTTGAATGTCGTGAAGGAAGCAGTTCCTCTGGAAGCTTCTTGAAGAC
AAACAACGTCTGTAGCGACCCTTTGCAGGCAGCGGAACCCCCACCTGGCGACA
GGTGCCTCTGCGGCCAAAAGCCACGTGTATAAGATACACCTGCAAAGGCGGCAC
AACCCCAGTGCCACGTTGTGAGTTGGATAGTTGTGGAAAGAGTCAAATGGCTCTC
CTCAAGCGTATTCAACAAGGGGCTGAAGGATGCCCAGAAGGTACCCCATTGTATG
GGATCTGATCTGGGGCCTCGGTGCACATGCTTTACATGTGTTTAGTCGAGGTTAA
AAAAAC

*Xba I*

GTCTAGGCCCCCCGAACCACGGGGACGTGGTTTTCCTTTGAAAAACACGATGATA
AGCTTGCCACAACCCGGGATCCTCTAGA
CCACCATGGTTCGACCATTGAACTGCATCGTCGCCGTGTCCCAAGATATGGGGAT
TGGCAAGAACGGAGACCTACCCTGGCCTCCGCTCAGGAACGAGTTCAAGTACTT
CCAAAGAATGACCACAACCTCTTCAGTGGAAGGTAAACAGAATCTGGTGATTATG
GGTAGGAAAACCTGGTTCTCCATTCCTGAGAAGAATCGACCTTTAAAGGACAGAA
TTAATATAGTTCTCAGTAGAGAACTCAAAGAACCACCACGAGGAGCTCATTTTCTT
GCCAAAAGTTTGGATGATGCCTTAAGACTTATTGAACAACGGAATTGGCAAGTAA
AGTAGACATGGTTTGGATAGTCGGAGGCAGTTCTGTTTACCAGGAAGCCATGAAT
CAACCAGGCCACCTCAGACTCTTTGTGACAAGGATCATGCAGGAATTTGAAAGTG

FIG 3C

ACACGTTTTTCCCAGAAATTGATTTGGGGAAATATAAACTTCTCCCAGAATACCCA
GGCGTCCTCTCTGAGGTCCAGGAGGAAAAAGGCATCAAGTATAAGTTTGAAGT

*Not I*

CTACGAGAAGAAAGACTAAGCGGCCGC...3' (SEQ ID No1)

FIG 3D

MEWSRVFIFLLSVTAGVHSQVQLQQSGAELVRPGTSVKVSCKASGYAFTNYLIEWVK
QRPGQGLEWIGVINPGSGGTNYNEKFKGKATLTADKSSSTAYMQLSSLTSDDSAVYF
CARDGPWFAYWGQGTLVTVSAAKTTAPSVYPLAPVCGDTTGSSVTLGCLVKGYFPE
PVTLTWNSGSLSSGVHTFPAVLQSDLYTLSSSVTVTSSTWPSQSITCNVAHPASSTKV
DKKIEPRGPTIKPCPPCKCPAPNLLGGPSVFIFPPKIKDVLMISLSPIVTCVVVDVSEDD
PDVQISWFVNNVEVHTAQTQTHREDYNSTLRVVSALPIQHQDWMSGKEFKCKVNNK
DLPAPIERTISKPKGSVRAPQVYVLPPPEEEMTKKQVTLTCMVTDFMPEDIYVEWTNN
GKTELNYKNTEPVLDSDGSYFMYSKLRVEKKNWVERNSYSCSVVHEGLHNHHTTKS
FSRTPGK (SEQ ID No2)

Figure 6

MHQTSMGIKMESQTLVFISILLWLYGADGNIVMTQSPKSMSMSVGERVTLTCKASENV
VTYVSWYQQKPEQSPKLLIYGASNRYTGVPDRFTGSGSATDFTLTISSVQAEDLADYH
CGQGYSYPYTFGGGTKLEIKRADAAPTVSIFPPSSEQLTSGGASVVCFLNNFYPKDIN
VKWKIDGSERQNGVLNSWTDQDSKDSTYSMSSTLTLTKDEYERHNSYTCEATHKTS
TSPIVKSFNRNEC (SEQ ID No3)

Figure 7

MHQTSMGIKMESQTLVFISILLWLYGADGNIVMTQSPKSMSMSVGERVTLTCKASENV
VTYVSWYQQKPEQSPKLLIYGASNRYTGVPDRFTGSGSATDFTLTISSVQAEDLADYH
CGQGYSYPYTFGGGTKLEIRRADAAPTVSIFPPSSEQLTSGGASVVCFLNNFYPKDIN
VKWKIDGSERQNGVLNSWTDQDSKDSTYSMSSTLTLTKDEYERHNSYTCEATHKTS
TSPIVKSFNRNEC (SEQ ID No4)

Figure 8

MHQTSMGIRMESQTLVFISILLWLYGADGNIVMTQSPRSMSMSVGERVTLTCRASEN
VVTYVSWYQQRPEQSPRLLIYGASNRYTGVPDRFTGSGSATDFTLTISSVQAEDLAD
YHCGQGYSYPYTFGGGTRLEIRRADAAPTVSIFPPSSEQLTSGGASVVCFLNNFYPKD
INVKWKIDGSERQNGVLNSWTDQDSKDSTYSMSSTLTLTKDEYERHNSYTCEATHKT
STSPIVKSFNRNEC (SEQ ID No5)

SEQUENCE LISTING

```
<160> NUMBER OF SEQ ID NOS: 5

<210> SEQ ID NO 1
<211> LENGTH: 3973
<212> TYPE: DNA
<213> ORGANISM: Artificial Sequence
<220> FEATURE:
<223> OTHER INFORMATION: recombinant mouse IgG2a mAB 17-1A antibody
      produced in CHO (Chinese Hamster Ovary) cells
<220> FEATURE:
<221> NAME/KEY: misc_feature
<222> LOCATION: (213)..(213)
<223> OTHER INFORMATION: n = a, g, c, t
<220> FEATURE:
<221> NAME/KEY: misc_feature
<222> LOCATION: (288)..(288)
<223> OTHER INFORMATION: n = a, g, c, t

<400> SEQUENCE: 1
ataggctagc ctcgagccac caccatgcat cagaccagca tgggcatcaa gatggaatca      60
```

```
cagactctgg tcttcatatc catactgctc tggttatatg gagctgatgg gaacattgta    120
atgacccaat ctcccaaatc catgtccatg tcagtaggag agagggtcac cttgacctgc    180
aaggccagtg agaatgtggt tacttatgtt tcntggtatc aacagaaacc agagcagtct    240
cctaaactgc tgatatatgg ggcatccaac cggtacactg gggtcccnga tcgcttcaca    300
ggcagtggat ctgcaacaga tttcactctg accatcagca gtgtgcaggc tgaagacctt    360
gcagattatc actgtggaca gggttacagc tatccgtaca cgttcggagg ggggaccaag    420
ctggaaataa aacgggctga tgctgcacca actgtatcca tcttcccacc atccagtgag    480
cagttaacat ctggaggtgc ctcagtcgtg tgcttcttga caacttcta ccccaaagac     540 atcaatgtca agtggaagat tgatggcagt gaacgacaaa atggcgtcct gaacagttgg    600
actgatcagg acagcaaaga cagcacctac agcatgagca gcaccctcac gttgaccaag    660
gacgagtatg aacgacataa cagctatacc tgtgaggcca ctcacaagac atcaacttca    720
cccattgtca agagcttcaa caggaatgag tgttagacgc gtggatccgc ccctctccct    780
cccccccccc taacgttact ggccgaagcc gcttggaata aggccggtgt gcgtttgtct    840
atatgtgatt ttccaccata ttgccgtctt ttggcaatgt gagggcccgg aaacctggcc    900
ctgtcttctt gacgagcatt cctaggggtc tttcccctct cgccaaagga atgcaaggtc    960 tgttaatgt cgtgaaggaa gcagttcctc tggaagcttc ttgaagacaa caacgtctg    1020 tagcgaccct ttgcaggcag cggaaccccc cacctggcga caggtgcctc tgcggccaaa  1080
agccacgtgt ataagataca cctgcaaagg cggcacaacc ccagtgccac gttgtgagtt   1140
ggatagttgt ggaaagagtc aaatggctct cctcaagcgt attcaacaag gggctgaagg    1200
atgcccagaa ggtaccccat tgtatgggat ctgatctggg gcctcggtgc acatgcttta    1260
catgtgttta gtcgaggtta aaaaaacgtc taggcccccc gaaccacggg gacgtggttt    1320
tcctttgaaa aacacgatga taatatggcc accaccatgg aatggagcag agtctttatc    1380
tttctcctat cagtaactgc aggtgttcac tcccaggtcc agttgcagca gtctggagct    1440
gagctggtaa ggcctgggac ttcagtgaag gtgtcctgca aggcttctgg atacgccttc    1500
actaattact tgatagagtg ggtaaagcag aggcctggac agggccttga gtggattggg    1560
gtgattaatc ctggaagtgg tggtactaac tacaatgaga agttcaaggg caaggcaaca    1620
ctgactgcag acaaatcctc cagcactgcc tacatgcagc tcagcagcct gacatctgat    1680
gactctgcgg tctatttctg tgcaagagat ggtccctggt ttgcttactg gggccaaggg    1740
actctggtca ctgtctctgc agccaaaaca acagcccccat cggtctatcc actggcccct    1800
gtgtgtggag atacaactgg ctcctcggtg actctaggat gcctggtcaa gggttatttc    1860
cctgagccag tgaccttgac ctggaactct ggatccctgt ccagtggtgt gcacaccttc   1920
ccagctgtcc tgcagtctga cctctacacc ctcagcagct cagtgactgt aacctcgagc    1980
acctggccca gccagtccat cacctgcaat gtggcccacc cggcaagcag caccaaggtg    2040
gacaagaaaa ttgagcccag agggcccaca atcaagccct gtcctccatg caaatgccca    2100
gcacctaacc tcttgggtgg accatccgtc ttcatcttcc ctccaaagat caaggatgta   2160
ctcatgatct ccctgagccc catagtcaca tgtgtggtgg tggatgtgag cgaggatgac   2220 ccagtgtcc agatcagctg gtttgtgaac aacgtggaag tacacacagc tcagacacaa    2280
acccatagag aggattacaa cagtactctc cgggtggtca gtgccctccc catccagcac    2340
caggactgga tgagtggcaa ggagttcaaa tgcaaggtca acaacaaaga cctcccagcg    2400
cccatcgaga gaaccatctc aaaacccaaa gggtcagtaa gagctccaca ggtatatgtc    2460
```

```
ttgcctccac cagaagaaga gatgactaag aaacaggtca ctctgacctg catggtcaca   2520
gacttcatgc ctgaagacat ttacgtggag tggaccaaca acgggaaaac agagctaaac   2580
tacaagaaca ctgaaccagt cctggactct gatggttctt acttcatgta cagcaagctg   2640
agagtggaaa agaagaactg ggtggaaaga aatagctact cctgttcagt ggtccacgag   2700
ggtctgcaca atcaccacac gactaagagc ttctcccgga ctccgggtaa atgagtcgac   2760
acgcgtcgag catgcatcta gggcggccaa ttccgcccct ctccctcccc ccccctaac    2820 gttactggcc gaagccgctt ggaataaggc cggtgtgcgt ttgtctatat gtgattttcc   2880
accatattgc cgtcttttgg caatgtgagg gcccggaaac ctggccctgt cttcttgacg   2940
agcattccta ggggtctttc ccctctcgcc aaaggaatgc aaggtctgtt gaatgtcgtg   3000
aaggaagcag ttcctctgga agcttcttga agacaaacaa cgtctgtagc gaccctttgc   3060
aggcagcgga accccccacc tggcgacagg tgcctctgcg gccaaaagcc acgtgtataa   3120
gatacacctg caaaggcggc acaaccccag tgccacgttg tgagttggat agttgtggaa   3180
agagtcaaat ggctctcctc aagcgtattc aacaaggggc tgaaggatgc ccagaaggta   3240
ccccattgta tgggatctga tctggggcct cggtgcacat gctttacatg tgtttagtcg   3300
aggttaaaaa aacgtctagg ccccccgaac cacggggacg tggttttcct ttgaaaaaca   3360
cgatgataag cttgccacaa cccgggatcc tctagaccac catggttcga ccattgaact   3420
gcatcgtcgc cgtgtcccaa gatatgggga ttggcaagaa cggagaccta ccctggcctc   3480
cgctcaggaa cgagttcaag tacttccaaa gaatgaccac aacctcttca gtggaaggta   3540
aacagaatct ggtgattatg ggtaggaaaa cctggttctc cattcctgag aagaatcgac   3600
ctttaaagga cagaattaat atagttctca gtagagaact caaagaacca ccacgaggag   3660 ctcatttct tgccaaaagt ttggatgatg ccttaagact tattgaacaa ccggaattgg   3720
caagtaaagt agacatggtt tggatagtcg gaggcagttc tgtttaccag gaagccatga   3780
atcaaccagg ccacctcaga ctctttgtga caaggatcat gcaggaattt gaaagtgaca   3840 cgttttttccc agaaattgat ttggggaaat ataaacttct cccagaatac ccaggcgtcc   3900
tctctgaggt ccaggaggaa aaaggcatca agtataagtt tgaagtctac gagaagaaag   3960
actaagcggc cgc                                                     3973
```

<210> SEQ ID NO 2
<211> LENGTH: 465
<212> TYPE: PRT
<213> ORGANISM: Artificial Sequence
<220> FEATURE:
<223> OTHER INFORMATION: recombinant mouse IgG2a mAB 17-1A antibody
produced in CHO (Chinese Hamster Ovary) cells

<400> SEQUENCE: 2

```
Met Glu Trp Ser Arg Val Phe Ile Phe Leu Leu Ser Val Thr Ala Gly
  1               5                  10                  15

Val His Ser Gln Val Gln Leu Gln Gln Ser Gly Ala Glu Leu Val Arg
                 20                  25                  30

Pro Gly Thr Ser Val Lys Val Ser Cys Lys Ala Ser Gly Tyr Ala Phe
             35                  40                  45

Thr Asn Tyr Leu Ile Glu Trp Val Lys Gln Arg Pro Gly Gln Gly Leu
         50                  55                  60

Glu Trp Ile Gly Val Ile Asn Pro Gly Ser Gly Gly Thr Asn Tyr Asn
 65                  70                  75                  80

Glu Lys Phe Lys Gly Lys Ala Thr Leu Thr Ala Asp Lys Ser Ser Ser
```

```
                    85                  90                  95
Thr Ala Tyr Met Gln Leu Ser Ser Leu Thr Ser Asp Asp Ser Ala Val
                100                 105                 110
Tyr Phe Cys Ala Arg Asp Gly Pro Trp Phe Ala Tyr Trp Gly Gln Gly
                115                 120                 125
Thr Leu Val Thr Val Ser Ala Ala Lys Thr Thr Ala Pro Ser Val Tyr
            130                 135                 140
Pro Leu Ala Pro Val Cys Gly Asp Thr Thr Gly Ser Ser Val Thr Leu
145                 150                 155                 160
Gly Cys Leu Val Lys Gly Tyr Phe Pro Glu Pro Val Thr Leu Thr Trp
                165                 170                 175
Asn Ser Gly Ser Leu Ser Ser Gly Val His Thr Phe Pro Ala Val Leu
            180                 185                 190
Gln Ser Asp Leu Tyr Thr Leu Ser Ser Ser Val Thr Val Thr Ser Ser
        195                 200                 205
Thr Trp Pro Ser Gln Ser Ile Thr Cys Asn Val Ala His Pro Ala Ser
    210                 215                 220
Ser Thr Lys Val Asp Lys Lys Ile Glu Pro Arg Gly Pro Thr Ile Lys
225                 230                 235                 240
Pro Cys Pro Pro Cys Lys Cys Pro Ala Pro Asn Leu Leu Gly Gly Pro
                245                 250                 255
Ser Val Phe Ile Phe Pro Pro Lys Ile Lys Asp Val Leu Met Ile Ser
                260                 265                 270
Leu Ser Pro Ile Val Thr Cys Val Val Asp Val Ser Glu Asp Asp
            275                 280                 285
Pro Asp Val Gln Ile Ser Trp Phe Val Asn Asn Val Glu Val His Thr
    290                 295                 300
Ala Gln Thr Gln Thr His Arg Glu Asp Tyr Asn Ser Thr Leu Arg Val
305                 310                 315                 320
Val Ser Ala Leu Pro Ile Gln His Gln Asp Trp Met Ser Gly Lys Glu
                325                 330                 335
Phe Lys Cys Lys Val Asn Asn Lys Asp Leu Pro Ala Pro Ile Glu Arg
                340                 345                 350
Thr Ile Ser Lys Pro Lys Gly Ser Val Arg Ala Pro Gln Val Tyr Val
            355                 360                 365
Leu Pro Pro Pro Glu Glu Glu Met Thr Lys Lys Gln Val Thr Leu Thr
        370                 375                 380
Cys Met Val Thr Asp Phe Met Pro Glu Asp Ile Tyr Val Glu Trp Thr
385                 390                 395                 400
Asn Asn Gly Lys Thr Glu Leu Asn Tyr Lys Asn Thr Glu Pro Val Leu
                405                 410                 415
Asp Ser Asp Gly Ser Tyr Phe Met Tyr Ser Lys Leu Arg Val Glu Lys
                420                 425                 430
Lys Asn Trp Val Glu Arg Asn Ser Tyr Ser Cys Ser Val Val His Glu
            435                 440                 445
Gly Leu His Asn His His Thr Thr Lys Ser Phe Ser Arg Thr Pro Gly
        450                 455                 460
Lys
465

<210> SEQ ID NO 3
<211> LENGTH: 243
<212> TYPE: PRT
<213> ORGANISM: Artificial Sequence
<220> FEATURE:
```

<223> OTHER INFORMATION: recombinant mouse IgG2a mAB 17-1A antibody
      produced in CHO (Chinese Hamster Ovary) cells

<400> SEQUENCE: 3

Met His Gln Thr Ser Met Gly Ile Lys Met Glu Ser Gln Thr Leu Val
1               5                   10                  15

Phe Ile Ser Ile Leu Leu Trp Leu Tyr Gly Ala Asp Gly Asn Ile Val
                20                  25                  30

Met Thr Gln Ser Pro Lys Ser Met Ser Met Ser Val Gly Glu Arg Val
            35                  40                  45

Thr Leu Thr Cys Lys Ala Ser Glu Asn Val Val Thr Tyr Val Ser Trp
        50                  55                  60

Tyr Gln Gln Lys Pro Glu Gln Ser Pro Lys Leu Leu Ile Tyr Gly Ala
65                  70                  75                  80

Ser Asn Arg Tyr Thr Gly Val Pro Asp Arg Phe Thr Gly Ser Gly Ser
                85                  90                  95

Ala Thr Asp Phe Thr Leu Thr Ile Ser Ser Val Gln Ala Glu Asp Leu
            100                 105                 110

Ala Asp Tyr His Cys Gly Gln Gly Tyr Ser Tyr Pro Tyr Thr Phe Gly
        115                 120                 125

Gly Gly Thr Lys Leu Glu Ile Lys Arg Ala Asp Ala Ala Pro Thr Val
130                 135                 140

Ser Ile Phe Pro Pro Ser Ser Glu Gln Leu Thr Ser Gly Gly Ala Ser
145                 150                 155                 160

Val Val Cys Phe Leu Asn Asn Phe Tyr Pro Lys Asp Ile Asn Val Lys
                165                 170                 175

Trp Lys Ile Asp Gly Ser Glu Arg Gln Asn Gly Val Leu Asn Ser Trp
            180                 185                 190

Thr Asp Gln Asp Ser Lys Asp Ser Thr Tyr Ser Met Ser Ser Thr Leu
        195                 200                 205

Thr Leu Thr Lys Asp Glu Tyr Glu Arg His Asn Ser Tyr Thr Cys Glu
210                 215                 220

Ala Thr His Lys Thr Ser Thr Ser Pro Ile Val Lys Ser Phe Asn Arg
225                 230                 235                 240

Asn Glu Cys

<210> SEQ ID NO 4
<211> LENGTH: 243
<212> TYPE: PRT
<213> ORGANISM: Artificial Sequence
<220> FEATURE:
<223> OTHER INFORMATION: recombinant mouse IgG2a mAB 17-1A antibody
      produced in CHO (Chinese Hamster Ovary) cells

<400> SEQUENCE: 4

Met His Gln Thr Ser Met Gly Ile Lys Met Glu Ser Gln Thr Leu Val
1               5                   10                  15

Phe Ile Ser Ile Leu Leu Trp Leu Tyr Gly Ala Asp Gly Asn Ile Val
                20                  25                  30

Met Thr Gln Ser Pro Lys Ser Met Ser Met Ser Val Gly Glu Arg Val
            35                  40                  45

Thr Leu Thr Cys Lys Ala Ser Glu Asn Val Val Thr Tyr Val Ser Trp
        50                  55                  60

Tyr Gln Gln Lys Pro Glu Gln Ser Pro Lys Leu Leu Ile Tyr Gly Ala
65                  70                  75                  80

Ser Asn Arg Tyr Thr Gly Val Pro Asp Arg Phe Thr Gly Ser Gly Ser
                85                  90                  95

```
Ala Thr Asp Phe Thr Leu Thr Ile Ser Ser Val Gln Ala Glu Asp Leu
            100                 105                 110

Ala Asp Tyr His Cys Gly Gln Gly Tyr Ser Tyr Pro Tyr Thr Phe Gly
        115                 120                 125

Gly Gly Thr Lys Leu Glu Ile Arg Arg Ala Asp Ala Ala Pro Thr Val
130                 135                 140

Ser Ile Phe Pro Pro Ser Ser Glu Gln Leu Thr Ser Gly Gly Ala Ser
145                 150                 155                 160

Val Val Cys Phe Leu Asn Asn Phe Tyr Pro Lys Asp Ile Asn Val Lys
                165                 170                 175

Trp Lys Ile Asp Gly Ser Glu Arg Gln Asn Gly Val Leu Asn Ser Trp
            180                 185                 190

Thr Asp Gln Asp Ser Lys Asp Ser Thr Tyr Ser Met Ser Ser Thr Leu
        195                 200                 205

Thr Leu Thr Lys Asp Glu Tyr Glu Arg His Asn Ser Tyr Thr Cys Glu
210                 215                 220

Ala Thr His Lys Thr Ser Thr Ser Pro Ile Val Lys Ser Phe Asn Arg
225                 230                 235                 240

Asn Glu Cys

<210> SEQ ID NO 5
<211> LENGTH: 243
<212> TYPE: PRT
<213> ORGANISM: Artificial Sequence
<220> FEATURE:
<223> OTHER INFORMATION: recombinant mouse IgG2a mAB 17-1A antibody
      produced in CHO (Chinese Hamster Ovary) cells

<400> SEQUENCE: 5

Met His Gln Thr Ser Met Gly Ile Arg Met Glu Ser Gln Thr Leu Val
1               5                   10                  15

Phe Ile Ser Ile Leu Leu Trp Leu Tyr Gly Ala Asp Gly Asn Ile Val
            20                  25                  30

Met Thr Gln Ser Pro Arg Ser Met Ser Met Ser Val Gly Glu Arg Val
        35                  40                  45

Thr Leu Thr Cys Arg Ala Ser Glu Asn Val Val Thr Tyr Val Ser Trp
    50                  55                  60

Tyr Gln Gln Arg Pro Glu Gln Ser Pro Arg Leu Leu Ile Tyr Gly Ala
65                  70                  75                  80

Ser Asn Arg Tyr Thr Gly Val Pro Asp Arg Phe Thr Gly Ser Gly Ser
                85                  90                  95

Ala Thr Asp Phe Thr Leu Thr Ile Ser Ser Val Gln Ala Glu Asp Leu
            100                 105                 110

Ala Asp Tyr His Cys Gly Gln Gly Tyr Ser Tyr Pro Tyr Thr Phe Gly
        115                 120                 125

Gly Gly Thr Arg Leu Glu Ile Arg Arg Ala Asp Ala Ala Pro Thr Val
130                 135                 140

Ser Ile Phe Pro Pro Ser Ser Glu Gln Leu Thr Ser Gly Gly Ala Ser
145                 150                 155                 160

Val Val Cys Phe Leu Asn Asn Phe Tyr Pro Lys Asp Ile Asn Val Lys
                165                 170                 175

Trp Lys Ile Asp Gly Ser Glu Arg Gln Asn Gly Val Leu Asn Ser Trp
            180                 185                 190

Thr Asp Gln Asp Ser Lys Asp Ser Thr Tyr Ser Met Ser Ser Thr Leu
        195                 200                 205
```

-continued

```
Thr Leu Thr Lys Asp Glu Tyr Glu Arg His Asn Ser Tyr Thr Cys Glu
    210                 215                 220

Ala Thr His Lys Thr Ser Thr Ser Pro Ile Val Lys Ser Phe Asn Arg
225                 230                 235                 240

Asn Glu Cys
```

US 8,034,338 B2

IMMUNOGENIC RECOMBINANT ANTIBODY

CROSS-REFERENCE TO RELATED APPLICATIONS

This application is the National Stage Application of International Patent Application No. PCT/EP2004/004059 filed on Apr. 16, 2004, which claims priority on application No. A 599/2003 filed in Austria on Apr. 17, 2003.

BRIEF SUMMARY OF THE INVENTION

The invention refers to an immunogenic recombinant antibody that is used for immunization of primates, in particular human beings. The invention further refers to a vaccine comprising the immunogenic recombinant antibody, and a method of producing the same.

BRIEF DESCRIPTION OF THE SEVERAL VIEWS OF THE DRAWING(S)

FIG. 1: Figure of the original pIRES expression vector

Figure 2:
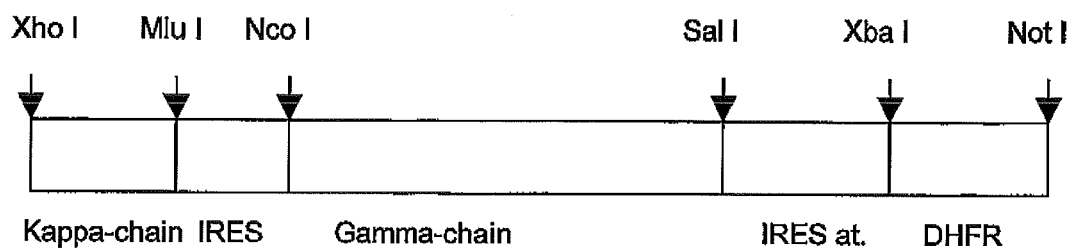

FIG. 2: Figure of the cloning cassette of the tri-cistronic mAb17-1A expression and DHFR selection construct.

FIG. 3: Sequence of the cloning cassette of the tri-cistronic mAb 17-1A expression and DHFR selection construct, introduced restriction sites bold and italic; KOZAK sequences underlined.

Figure 4:
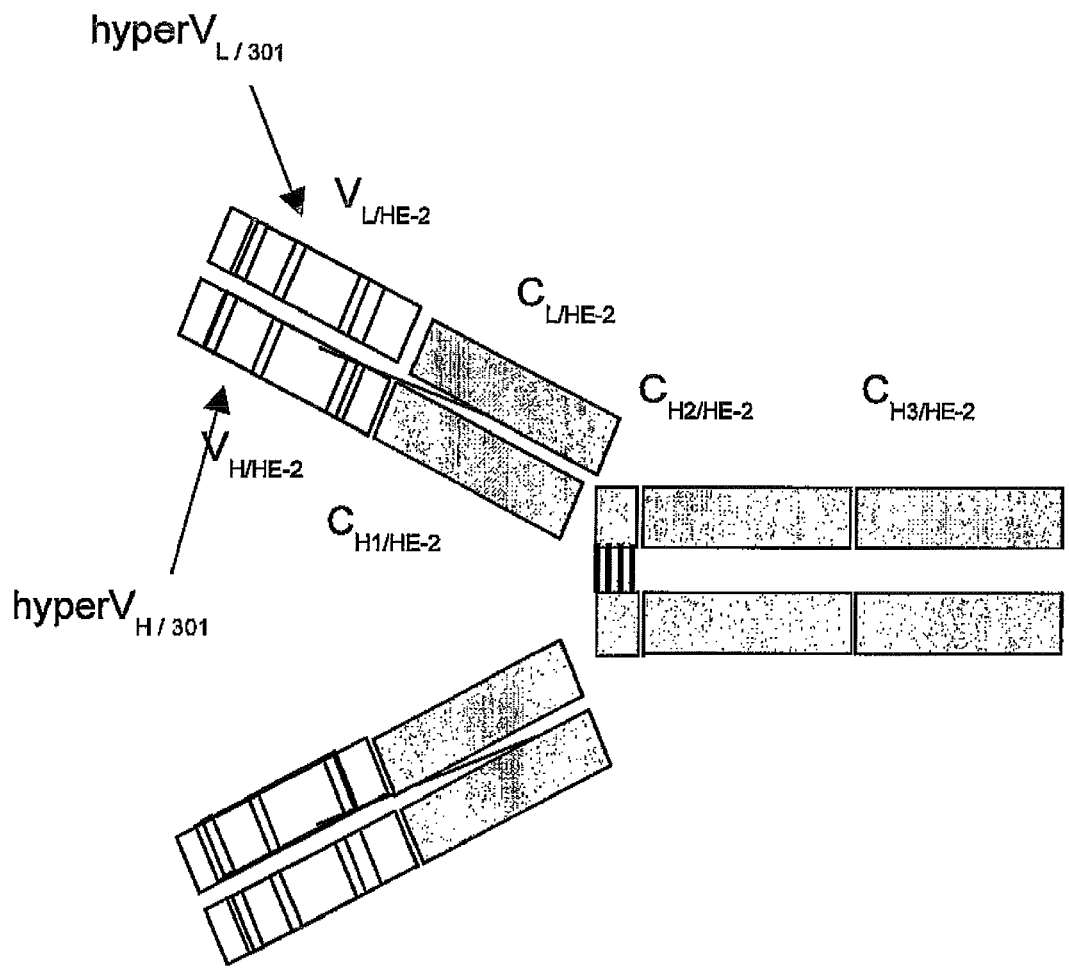

FIG. 4: Figure of an IgG2a Le-Y antibody

Figure 5:
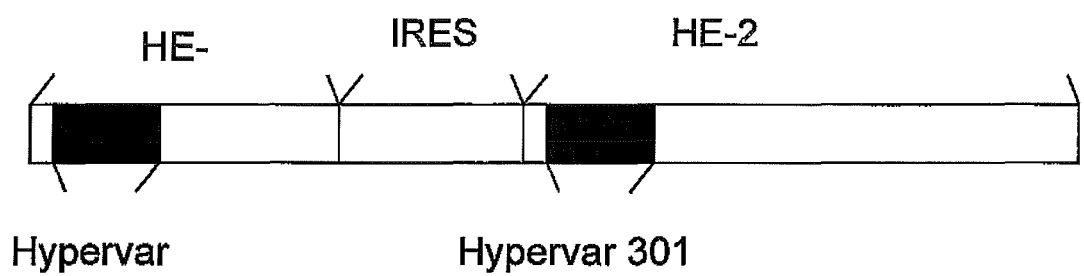

FIG. 5: Molecular biological IgG2a Le-y antibody construct

FIG. 6: amino acid sequence of mAb17-1A gamma

FIG. 7: Amino acid sequence of mAb17-1A kappa

FIG. 8: Amino acid sequence of mAb17-1A kappa with Arginine instead of Lysine at position 146

Figures 9, 10:
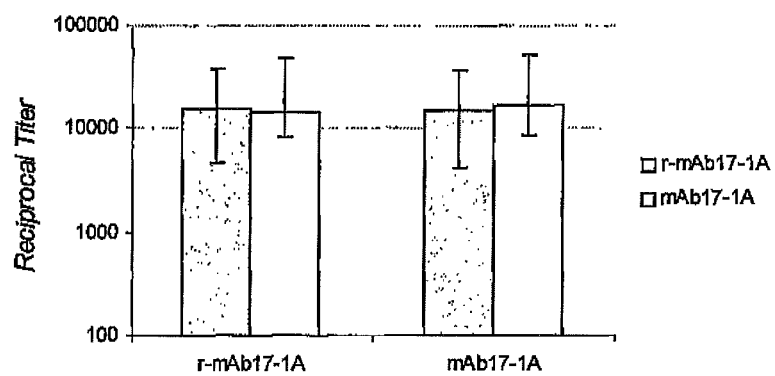

FIG. 9: Amino acid sequence of mAb17-1A kappa with Arginine replacements outside the CDRs FIG. 10: Cross-comparative ELISA analysis. Geometric means (4 animals per group) and CI (95%) are shown.

DETAILED DESCRIPTION OF THE INVENTION

The invention refers to an immunogenic recombinant antibody that is used for immunization of primates, in particular human beings. The invention further refers to a vaccine comprising the immunogenic recombinant antibody, and a method of producing the same.

Monoclonal antibodies (MAB) have been widely used for immunotherapy of a variety of diseases, among them infectious and autoimmune disease, as well as conditions associated with tumours or cancer. Using hybridoma technology MAB directed against a series of antigens have been produced in a standardized manner. A multitude of tumor-associated antigens (TAAs) are considered suitable targets for MAB and their use for the diagnosis of cancer and therapeutic applications. TAAs are structures that are predominantly expressed on the cell membrane of tumor cells and thus allow differentiation from non-malignant tissue.

Whether human TAAs detected by xenogeneic MABs are capable of inducing an antitumor immune response in cancer patients, and whether such antigens are indeed related to the response to autologous tumors in cancer patients, depends on the nature of the respective TAA and is still not fully understood. TAAs which are either naturally immunogenic in the syngeneic host or can be made immunogenic might potentially be used to induce antitumor immunity for therapeutic and possibly prophylactic benefit.

For passive immunotherapy MABs are administered systemically to a patient in a suitable amount to directly bind to a target. Thus an immune complex is formed and through a series of immune reactions the cell or organism afflicted with the target is killed. The therapeutic effect is depending on the concentration of the MABs in the circulation and the biological half-life, which is usually quite short. It is therefore necessary to repeat the administration within an appropriate timeframe. If xenogeneic MABs, such as murine antibodies are used, adverse reactions are however expected, possible leading to anaphylactic shock. Therefore, such immunotherapies are employed for a limited time only.

Active immunization regimens activate the immune system of patients in a specific way. Following the administration of an antigen that resembles a specific target the patients humoral and T-cell specific immune response induces defense mechanisms to combat the target in vivo. For active immunization these antigens are usually presented in an immunogenic formulation to provide a vaccine. Antigens mimicking the targets have either similarities in the primary and secondary sequence of the targets or fragments thereof. Mimotopes or mimotopic antigens, however, have similarities in the tertiary structure of the target.

Exemplary mimotopes are anti-idiotypic antibodies or mimotopic antibodies that imitate the structure of an antigen, which is considered as target for the immune system. Idiotypic interactions strongly influence the immune system. The unique antigenic determinants in and around the antigen-combining site of an immunoglobulin (Ig) molecule, which make one antibody distinct from another, are defined as idiotopes. All idiotopes present on the variable portion of an antibody are referred to as its idio-type (id). The molecular structure of an idiotype has been localized to both the complementary determining regions and the framework regions of the variable domain and is generally but not always contributed to by both the heavy and the light chains of an immunoglobulin in specific association.

Idiotypes are serologically defined entities. Injection of an antibody (Ab1) into a syngeneic, allogeneic, or xenogeneic recipient induces the production of anti-idiotypic antibodies (Ab2). With regard to idiotype/anti-idiotype interactions a receptor-based regulation of the immune system was postulated by Niels Jerne (Ann. Immunol. 125C, 373, 1974). His network theory considers the immune system as a collection of 1 g molecules and receptors on T-lymphocytes, each capable of recognizing an anti-genic determinant (epitope) through its combining site (paratope), and each capable of being recognized by other antibodies or cell-surface receptors of the system through the idiotopes that it displays.

Many studies have indeed demonstrated that idiotypic and anti-idiotypic receptors are present on the surface of both B- and T-lymphocytes as well as on secreted antibodies. An overview about anti-idiotypic antibodies used for the development of cancer vaccines is presented by Herlyn et al. (in vivo 5: 615-624 (1991)). The anti-idiotypic cancer vaccines contain either monoclonal or polyclonal Ab2 to induce anti-tumor immunity with a specificity of selected TAA.

When the binding between Ab1 and Ab2 is inhibited by the antigen to which Ab1 is directed, the idiotype is considered to be binding-site-related, since it involves a site on the antibody variable domain that is engaged in antigen recognition. Those idiotypes which conformationally mimic an antigenic epitope are called the internal image of that epitope. Since both an Ab2 and an antigen bind to the relevant Ab1, they may share a similar three-dimensional conformation that represents the internal image of the respective antigen. Internal image anti-idiotypic antibodies in principle are substitutes for the antigen from which they have been derived via the idiotypic network. Therefore these surrogate antigens may be used in active immunization protocols. The anti-idiotypic antibodies offer advantages if the original antigen is not sufficiently immunogenic to induce a significant immune response. Appropriate internal image anti-idiotypic antibodies that mimic a non-immunogenic carbohydrate antigen are especially useful for certain vaccination approaches.

Tumor associated antigens are often a part of "self" and evoke a very poor immune response in cancer patients. In contrast, internal image anti-idiotypic antibodies expressing three-dimensional shapes, which resemble structural epitopes of the respective TAA, are recognized as foreign molecules in the tumor-bearing host.

The immune response raised by therapeutic or even prophylactic immunization with appropriate anti-id MABs, thus may cause anti-tumor immunity.

Mimotopic antibodies are alike anti-idiotypic antibodies. They too resemble a target structure and may possibly activate the immune system against the target. The EP-B1-1 140 168 describes mimotopic antibodies against human cellular membrane antigens to produce antitumor immunity in cancer patients. These antibodies are directed against the EpCAM, NCAM or CEA antigens; each of these targets is well known to be tumor associated.

Therapeutic immunization against cancer with MABs may be especially successful in earlier stages of the disease: At the time of surgery of a primary tumor, frequently occult single tumor cells already have disseminated in various organs of the patient. These micrometastatic cells are known to be the cause for the later growth of metastases, often years after diagnosis and surgical removal of all clinically proven tumor tissue. So far in almost all cases metastatic cancer of epithelial origin is incurable.

Therefore an effective treatment of "minimal residual cancer", e.g. destruction of occult disseminated tumor cells or micrometastatic cells in order to prevent the growth of metastases is an urgent medical need. At these stages of the disease (adjuvant setting) conventional chemotherapeutic approaches are rather unsuccessful. However, specific antitumor immunity at the time of minimal residual disease can be obtained by immunization with appropriate MAB. Micrometastatic cells may thus be selectively eliminated by the immune system, leading to an increased relapse-free survival time.

Monoclonal antibodies with the specificity of BR55-2 (disclosed in e.g. Wistar EP 285 059, M. Blaszcyk-Thurin et al., J. Biol. Chem. 262 (1987) 372-379, or Z. Steplewski et al., Hybridoma 9 (1990) 201-210) bind to the Lewis Y6 antigen, a carbohydrate determinant selectively expressed on a majority of human solid tumors. Based on their properties antibodies BR55-2 can be used for passive immunotherapy of epithelial cancer.

The tumor associated Lewis Y oligosaccharide determinant, which is also expressed during certain stages of embryonic development, is almost not immunogenic by itself. However, monoclonal anti-idiotypic antibodies (Ab2) against BR55-2 (Ab1) with internal image properties by resembling structural epitopes of the Lewis Y antigen are useful for induction of a protective antitumor immunity, particularly in earlier stages of the disease (EP-B1-0 644 947).

Monoclonal anti-idiotypic antibodies (Ab2) against BR55-2 (Ab1) with internal image properties are described in EP-B1-0 644 947 to be used for inducing immunity against both free HIV and HIV-infected cells.

In addition to its expression on cancer of epithelial origin the Lewis Y carbohydrate antigen is also involved in the pathogenesis of infection with Human Immunodeficiency Virus (HIV). HIV-infected cells in vitro and in vivo express on their surface an altered glycosylation pattern, namely the Lewis Y carbohydrate determinant. This antigen normally occurs only during certain fetal development stages and is also associated with a variety of malignancies. Expression on HIV-infected cells may reflect their altered differentiation status induced by retroviral transformation. The Lewis Y oligosaccharide represents a specific host response expressed both on HIV-infected cells and free HIV-particles.

EpCAM (Epithelial Cell Adhesion Molecule) is expressed on nearly all tumors of epithelial origin, but also occurs on a large number of normal epithelial tissue or epithelial cells. It has been characterized as a self-adhesion molecule and is classified as a pan-epithelial adhesion antigen (J. Cell Biol. 125: 437 (1994)). As a membrane-anchored glycoprotein it strongly interacts in cell-to-cell adhesion in cancerous tissues.

Human epithelial antigen EpCAM derived peptides are proposed for treatment or prophylaxis of EpCAM associated cancers, for induction of cytotoxic T lymphocyte response effective against EpCAM positive tumor cells and for diagnostic purposes (WO-A1-97/15597).

U.S. Pat. No. 6,444,207 B1 describes an immunotherapy of tumors with a hybridoma derived monoclonal antibody against the 17-1A antigen, which is a determinant of the EpCAM molecule. Multiple doses of about 400 mg or more are administered for passive immunotherapy of gastrointestinal cancer.

EP-B1-1 140 168 describes an immunogenic formulation of HE2, an EpCAM specific murine IgG2a antibody. Immunization studies proved the induction of a strong antigen specific immune response cross-reacting with EpCAM and activating complement factors to induce tumor cell lysis. Rhesus monkey studies and clinical data indicated a high immunogenicity of the HE2 immunization antigen.

The expression of recombinant proteins in higher eukaryotic cells represents an essential tool in modern biology. The refinement of mammalian gene expression vectors enabled the progress in diverse scientific fields (Makrides, Protein Expression and Purification 17: 183-202 (1999)). Due to the increased demand for human antibodies to be used for human therapy, studies concerning the suitable cell line for high yield production of such complex molecules have been performed. Human or human-mouse hetero-hybridomas often have some limitations such as low growth rates and high serum requirements. This has led to the alternative use of recombinant cells to produce recombinant antibodies with the advantages of selection of cell lines for transfection, control of the antibody isotype, control of expression using strong promoters, etc (Strutzenberger et al., J Biotechnology 69 (2-3): 215-26 (1999)). The standard model of protein translation applies to the vast majority of eukaryotic mRNAs and involves ribosome entry at the 5'-cap structure followed by scanning of the mRNA in 5'-to 3'direction until the initiation codon is reached. In the field of IgG expression, the biomolecule is assembled by 4 correctly folded subunits. Amount and localization of these different subunits strongly influences folding by self-organization of the expression product and therefore its biological activity.

U.S. Pat. No. 6,331,415 B1 describes methods of producing recombinant immunoglobulins, vectors and transformed host cells. One or more vectors are used to produce both heavy and light chains of an antibody, or fragments thereof in a single cell. Disclosed hosts are bacterial cells or yeast.

Due to different amounts of the genes encoding the immunoglobulin subunits integrated into the host genome, misfolded and biological inactive expression products may occur. It is required that two different genes are transcribed and four polypeptide chains are assembled in a balanced manner. Therefore oligocistronic expression systems are described for the production of antibodies (WO-A1-98/11241). The oligocistronic expression vectors are under the control of a strong promoter/enhancer unit, a selection marker gene and at least two IRES (Internal Ribosomal Entry Site) elements.

Bi-cistronic expression vectors may be suitable for a balanced expression of the polypeptide chains. IRES elements are usually derived from encephalomyocarditis virus, foot-and-mouth disease virus or poliovirus. Ribosomes are able to enter a mRNA molecule at the IRES sites and initiate the translation of multiple open reading frames on the same mRNA strand. The major advantage of those constructs is the possibility to express different genes under the control of a single promoter independent from their integration sites into the host genome. Selection markers integrate independent of the desired genes to be expressed into the host genome (Rees S. et al., BioTechniques, 1996, 20, 103-110).

In order to overcome possible problems of repeated use of murine antibodies for treating humans, mouse/human chimeric MABs can be generated by combining the variable domains of a parent murine MAB of choice with human constant regions. To further improve the properties of MABs for use in passive immunotherapy, "fully humanized" antibodies are constructed by recombinant DNA technology. Minimal parts of a parent mouse antibody that comprise the complementarity determining regions (CDRs), are combined with human variable region frameworks and human constant regions. For the design and construction of these "fully humanized" MABs, sequence homology and molecular modelling is used to select a combination of mouse and human sequence elements that would further reduce immunogenicity while retaining the binding properties.

Schneider et al (Proc Natl Acad Sci USA 85: 2509-13 (1988)) describe genetically engineered immunoglobulins revealing structural features that control segmental flexibility of an immunoglobulin. The proteins studied were hybrids of relatively rigid isotype (mouse IgG1) and a relatively flexible one (mouse IgG2a).

It was the object of the invention to provide preparations of monoclonal antibodies with improved immunogenic properties to be used for immunizing patients, in particular cancer patients.

According to the invention there is provided an immunogenic recombinant antibody that is designed for immunization of primates. The antibody comprises at least part of a murine IgG2a subtype amino acid sequence and a mammalian glycosylation. The antibody according to the invention is obtained by recombinant nucleic acid technology, in particular recombinant DNA technology, to produce the immunogenic antibody in a standardized manner.

Immunization studies surprisingly revealed that the murine IgG2a part is critical to design an immunogenic antibody, in particular when compared to IgG1 antibodies. In the following the immunogenic antibody comprising at least part of the IgG2a amino acid sequence according to the invention is called "IgG2a immunogenic antibody".

The term "immunogenic" defines any structure that leads to an immune response in a specific host system. For example, a murine antibody or fragments thereof is highly immunogenic in humans, especially when combined with adjuvants.

An immunogenic antibody according to the invention may have immunogenicity by its specificity or by its structure. The immunogenic antibody can induce immunogenicity also when being denatured or when conjugated to certain structures or carriers.

The humoral immune response induced by the IgG2a immunogenic antibodies according to the invention has significantly improved in terms of the quantity of specific antibody induced by the patients and the specificity against selected targets and epitopes. The improved immune response surprisingly turned out to be dependent on the glycosylation pattern of the antibody. A non-glycosylated or deglycosylated variant of the IgG2a immunogenic antibody according to the invention can also induce an immune response, although the immune response is lower and/or the immunization kinetics is delayed compared to a glycosylated antibody. A similar titer endpoint can be deserved but individuals take significantly longer to reach plateau values of immunization antigen specific titers.

It was surprisingly found by the inventors that a recombinant antibody expressed in hamster or human cells shows a similar immunogenicity than an antibody expressed by murine hybridoma cells. This is of particular relevance for antibodies that are used for immunization purposes.

It was well known in the art that immunogenicity of antigens is highly influenced by the glycosylation pattern. In case of tumor vaccines a major prerequisite for their success is their uptake by antigen-presenting cells (APCs) and transport of these APCs to the draining lymph nodes where the processed and presented tumor-associated antigens activate tumor-specific naïve T-cells. This immunogenicity is highly increased by α-Gal epitopes (Gal α 1,3Galβ1,4GlcNAc-R, Galili-epitopes). The α-gal-epitope is produced in large amounts in non-primate mammals and New world monkeys, but it is completely absent in humans, apes and Old World monkeys, because these species lack ☐1,3Galactosyltransferase. Also CHO cells do not express these Galili epitopes (La Temple D. C. et al., 1999, Cancer Res., 59, 3417-3423, Winand R. J. et al, J. Immunol., 1993, 151, 3923-3934).

Nevertheless, CHO (Chinese hamster ovary) or human glycosylation has proven to provide an immunogenic antibody that can be superior to a non-glycosylated variant. Glycosylation patterns of rodents or those of primates, among them human or chimpanzees, are preferred. Preferably the rodents are non-murine.

The antibody may have a murine amino acid sequence or any other mammalian amino acid sequence that is combined with the murine IgG2a part. Preferable mammalian sequences are human or humanized or human/murine chimeric or murine sequences. Among the preferred antibodies are thus murine, chimeric or humanized and "fully humanized" antibodies.

The IgG2a immunogenic recombinant antibody according to the invention can be an antibody directed against a tumor associated antigen (TAA) or a part or fragment thereof.

The IgG2a immunogenic antibody according to the invention can also be an anti-idiotypic antibody (Ab2) or a mimotopic Ab1 antibody. Either the functional antibody is provided, or fragments, variants and derivatives thereof. A functional antibody consists of two types of polypeptide chains that can be cleaved into further subunits, the two large, heavy chains and two light chains. The polypeptides are connected by disulfide bridges and non-covalent bounds. The light chains are either lambda or kappa chains. Preferably the functional antibody has a natural specificity and can activate the complement system. More preferably it has neutralizing activity.

The mimotopic antibody according to the invention preferably mimics an antigen or target that is recognized by the idiotype of the antibody itself. The idiotypic antibody (Ab1) is preferably directed against a tumor-associated antigen, TAA. The preferred Ab2 antibody according to the invention is directed against the idiotype of an antibody specific for a TAA.

The IgG2a immunogenic antibody according to the invention may present the specific epitopes, which are either present in the mammalian original amino acid sequence or introduced by antibody engineering, including recombination, conjugation and derivatization techniques.

Generally, a molecular modelling to redesign the antibody according to the invention can be carried out. The possible variations are many and range from the changing of just one or a few amino acids to the complete redesign of, for example, the constant region. Changes in the constant region will, in general, be made in order to improve the cellular process characteristics, such as complement fixation, interaction with membranes, and other effector functions. Changes in the variable region will be made in order to improve the antigen binding characteristics. These alterations can be made by standard recombinant techniques and also by oligo-directed mutagenesis techniques (Dalbadie-McFarland et al., Proc. Natl. Acad. Sci (USA), 79:6.409 (1982), WO 91/17177, Berstein et al., J. Mol. Biol., 112:535-542 (1977)

The amino acid sequence of the IgG2a antibody according to the invention can be identical to the mammalian original amino acid sequence but can also include amino acid variations leading to an IgG2a antibody with immunogenic properties comparable, preferably identical to those of the IgG2a antibody containing the mammalian original amino acid sequence.

For example, the amino acid variations can be a variation of one or more amino acids, preferably not more than ten amino acids, more preferably not more than 5 amino acids, most preferably one amino acid compared to the sequence of an IgG2a antibody as known from Sun et al. (Proc Natl Acad Sci USA, 84:214-8 (1987)) or according to FIG. 6 or 7.

The amino acid of the kappa chain can be as shown in FIG. 8. Alternatively there is an amino acid variation within the kappa chain of the antibody, preferably approx. 10 amino acids after the end of the 3rd complementarity determining region (CDR). The amino acid variation can be any amino acid, preferably the replacement of a lysine by an arginine.

Alternatively there can be replacements of additional and/or other lysine-residues within the kappa chain of the antibody by arginine, for example at positions 9, 38, 53, 68, 74, 132 of FIG. 9.

These amino acid replacements can lead to the positive effect that the variable region of the antibody contains less primary amines which are preferentially used for covalent protein immobilization or coupling of functional groups like carbohydrates via primary amines.

The term "epitope" defines any region of a molecule that can be recognised by specific antibody or that provoke the formation of those specific antibodies. Epitopes may be either conformational epitopes or linear epitopes.

Preferred epitopes presented by the IgG2a immunogenic antibody are derived from antigens specific for epithelial tumors (tumor associated antigens), and frequently expressed in breast cancer, gastrointestinal, colorectal, prostate, pancreatic, and ovary and lung cancer, either being small cell lung cancer (SCLC) or non small cell lung cancer (NSCLC). The preferred epitopes especially induce humoral immune response and the formation of specific antibodies in vivo. The antibodies according to the invention preferably also induce T cell specific response. This can preferably be induced by coupling carbohydrate residues on the antibody according to the invention, such as Lewis antigens, e.g. Lewis x-, Lewis b-und Lewis y-structures, also sialylated Lewis x-structures, GloboH-structures, KH1, Tn-antigen, TF-antigen and alpha-1-3-galactosyl-epitope.

Among the preferred epitopes are protein epitopes that are expressed on malignant cells of solid tumors, e.g. TAG-72, MUC1, Folate Binding Protein A-33, CA125, HER-2/neu, EGF-receptors, PSA, MART etc. Moreover, T cell epitope peptides or mimotopes of such T cell epitopes may be presented by the antibody according to the invention. Suitable epitopes are usually expressed in at least 20% of the cases of a particular disease or cancer, preferably in at least 30%, more preferably in at least 40%, most preferably in at least 50% of the cases.

According to the invention there are preferred carbohydrate epitopes that are derived from tumor associated aberrant carbohydrate structures, such as Lewis antigens, e.g. Lewis x-, Lewis b-und Lewis y-structures, also sialylated Lewis x-structures, GloboH-structures, KH1, Tn-antigen, Sialyl-Tn, TF-antigen and alpha-1-3-galactosyl-epitope.

The preferred TAA targets or epitopes are selected from the group of determinants derived from the group of antigens consisting of peptides or proteins, such as EpCAM, NCAM, CEA and T cell peptides, carbohydrates, such as aberrant glycosylation patterns, Lewis Y, Sialyl-Tn, Globo H, or glycolipids, such as GD2, GD3 und GM2. Antibodies according to the invention can have or mimic an epitope of any such TAA, and, at the same time, are directed against another or the same TAA, for example a mimotopic antibody directed against a cellular adhesion molecule, such as EpCAM, NCAM or CEA. These antibodies can be defined as bi-epitopic antibodies or bi-epitopic immunization antigens.

Additionally the antibody according to the invention can contain a mimotope or mimotopic antigen(s) or antigenic structure(s) triggering immune response specific for tumor associated antigens, for example epithelial cell specific adhesion molecules or tumor associated carbohydrate structures. For example, the IgG2a antibody according to the invention induces the development of Ep-CAM specific antibodies. Preferably, the antibody according to the invention can contain an EpCAM specific hinge region.

It was found that the amino acid sequence of the IgG2a hinge region has structures of homology compared to the Ep-CAM amino acid sequence. The amino acid sequence numbering used is identical to the numbering as published by Strnad J. et al., Cancer Res., 49 (1989), 314-317. These homologies might influence the specificity of the antibody according to the invention for EpCAM. For example, amino acids 36 to 42, amino acids 117 to 131, amino acids 124 to 134, amino acids 144 to 160 show significant homology between 29% and 57% to regions within the hinge region of IgG2a antibodies.

Further preferred antigens or targets are derived from antigens of infectious agents such as viral, bacterial, fungal, transmissible spongiform encephalitis agents (TSE) or parasitic agents. Among the preferred antigens or targets are determinants of glycosylation patterns of the virus and infected cells, such as Lewis Y glycosylation of infected HIV cells.

There are methods known in the art to define suitable antigens, determinants and related epitopes necessary to produce the peptides, polypeptides or proteins, related nucleic acids, lipoproteins, glycolipids, carbohydrates or lipids, which are derived from TAA or infectious agents. Without undue experiments the IgG2a immunogenic antibody is thus designed and engineered by selecting the suitable Ab1 mimotopic or Ab2 antibody, optionally modifying its amino acid sequence, and expressing it in a suitable recombinant host cell.

The IgG2a immunogenic antibody according to the invention may be specifically designed to have characteristics of composite or hybrid antibodies to combine at least two types or subtypes of immunoglobulins. The preferred bi-isotypic antibody is for instance selected from variable regions of IgG1 or IgG3 antibodies that care switched to the IgG2a subtype amino acid sequence. The IgG2a subtype amino acid sequence is either inserted into the sequence of the parent antibody or substitutes for similar parts of the parent antibody. The preferred location of the IgG2a sequence is in the constant region of the antibody, most preferred in at least one of the regions selected from the group consisting of the CL, CH1, hinge, CH2 and CH3 regions. Most preferred is an antibody wherein the IgG2a region is within the hinge region.

The best mode of the IgG2a immunogenic antibody refers to an anti-idiotypic antibody to monoclonal antibodies produced by ATCC HB 9324 or ATCC HB 9347, hybridised with at least part of a murine amino acid sequence of an IgG2a antibody. The IgG2a immunogenic antibody is for example a construct of an anti-idiotypic Lewis-Y mimicking hypervariable region and the highly immunogenic mouse IgG2a constant regions to build a functional antibody.

The invention further encompasses vaccines for immunization purposes, which comprise the IgG2a immunogenic antibody in a pharmaceutical formulation. The pharmaceutical formulation preferably contains auxiliary agents or adjuvants to improve the quality of an injection preparation in terms of safety, tolerability and immunogenicity. The design of the vaccine depends on the primates that are treated, among them specifically human beings or chimpanzees.

The vaccines according to the invention may be suitably used for the prophylaxis and therapy of cancer associated diseases, e.g. metastatic disease in cancer patients. The vaccine according to the invention specifically modulates antigen presenting cells in vivo or ex vivo, thus generating immune response to the epitope that is targeted by the IgG2a immunogenic antibody.

A vaccine according to the invention typically contains the IgG2a immunogenic antibody at low concentrations. The immunogenic amount often is ranging between 0.01 μg and 10 mg/single dose. Depending on the nature of the antibody, the immunogenicity may be altered by xenogenic sequences or derivatization of the antibody. Besides, the use of adjuvants further increases the immunogenicity of the IgG2a antibody. The immunogenic dose of an antibody suitably formulated with an adjuvant is thus preferably ranging between 0.01 μg and 750 μg/single dose, most preferably between 100 μg and 500 μg/single dose. A vaccine designed for depot injection will however contain far higher amounts of the IgG2a immunogenic antibody, e.g. at least 1 mg up to 10 mg/single dose. The immunogen is thus delivered to stimulate the immune system over a longer period of time.

The vaccine according to the invention usually is provided as ready-to-use preparation in a single-use syringe containing a volume of 0.01 to 1 ml, preferably 0.1 to 0.75 ml. The vaccine solution or suspension thus provided is highly concentrated. The invention further relates to a kit for vaccinating patients, which comprises the vaccine and suitable application devices, such as a syringe, injection devices, pistols. etc.

The vaccine is specifically formulated to produce a pharmaceutical preparation suitable for subcutaneous, intramuscular, intradermal or transdermal administration. Another possible route is the mucosal administration, either by nasal or peroral vaccination. If solids are used to prepare the pharmaceutical formulation the IgG2a immunogenic antibody is either administered as adsorbate or in suspension with the solids. Particular embodiments contain aqueous media for suspending the formulation or for solutions of the IgG2a immunogenic antibody to provide a liquid vaccine.

The vaccine is usually storage stable at refrigerating temperature. However, preservatives, such as thimerosal or other agents of improved tolerability may be used to improve its storage stability to enable prolonged storage times even at elevated temperatures up to room temperature. The vaccine according to the invention may also be provided in the frozen or lyophilized form, which is thawed or reconstituted on demand.

Preferred pharmaceutical formulations contain pharmaceutically acceptable carrier, such as buffer, salts, proteins or preservatives.

Exemplary adjuvants improving the efficacy of the vaccine according to the invention are aluminium hydroxide (alum gel) or aluminium phosphate, such as growth factors, lymphokine, cytokines, like IL-2, IL-12, GM-CSF, gamma interferon, or complement factors, e.g. C3d, liposomal preparations and formulations of additional antigens that are strong immunogens, such as tetanus toxoid, bacterial toxins, like pseudomonas exotoxins, *Bacillus calmette* Guerin (BCG) and derivatives of Lipid A.

In addition methods for producing antibody conjugates or denatured vaccine components may be employed to increase the immunogenicity of the IgG2a immunogenic antibody. Mixtures of the IgG2a immunogenic antibody and further vaccine antigens, in particular different anti-idiotypic antibodies, may serve for simultaneous vaccination.

The IgG2a immunogenic antibody is produced by genetic engineering as a recombinant molecule. Suitable host cells are CHO (Chinese hamster ovary) cells, BHK (baby hamster kidney) cells, HEK (human embryonic kidney) cells or the like. In any case the translated antibody thus obtains the glycosilation pattern of the host cell, which is critical to the immunogenicity of the antibody. If a host cell is selected that produces no glycosylation (such as bacterial cells, like *E. coli*) the antibody may be glycosylated by chemical or enzymatic means. The glycosylation pattern may be altered by common techniques.

Specific host cells may be selected according to their capability to produce a glycosylated expression product. Host cells could also be modified to produce those enzymes that are required for a specific glycosylation (Glycoconj. J. (1999), 16: 81).

Host cells expressing the antibody according to the invention are preferably cultivated without using serum or serum components. Common cultivation media may contain bovine serum, thus introducing bovine immunoglobulins into the harvested medium. Those bovine immunoglobulins or IgG may be difficult to separate from the expression product, which is the IgG2a immunogenic antibody according to the invention. Thus, the expression product is preferably obtained by cultivating host cells in a serum free medium, i.e. without the use of bovine serum, to produce an antibody devoid of bovine IgG, as measured by HPLC methods.

The IgG2a immunogenic antibody may have a native structure of a functionally intact antibody. However, it might be advantageous to produce an antibody derivative, preferably selected from the group of antibody fragments, conjugates or homologues. Preferred derivatives contain at least parts of the Fab fragment, most preferably together with at least parts of the F(ab')2 fragment and/or parts of the hinge region and/or parts of the Fc region of a lambda or kappa antibody. These fragments may be produced according to methods known from prior art, e.g. cleaving a monoclonal antibody with proteolytic enzymes such as papain or pepsin, or by recombinant methods. These Fab and F(ab)2 fragments may also be prepared by means of phage display gene library (Winter et al., 1994, Ann. Rev. Immunol., 12:433-455). The IgG2a immunogenic antibody according to the invention is usually of an IgG, IgM or IgA type.

Moreover, a single chain antibody derivative might be used as IgG2a immunogenic antibody according to the invention.

The preferred method for producing an antibody according to the invention makes use of a multicistronic antibody-expression construct to be used in a CHO, BHK or primate expression system. The construct according to the invention contains at least a nucleotide sequence encoding a kappa light chain and at least a nucleotide sequence encoding a gamma heavy chain, wherein at least one of the nucleotide sequences encoding a kappa light chain or gamma heavy chain comprises a nucleotide sequence encoding at least part of a murine IgG2a subtype amino acid sequence, and at least two IRES elements. Thus, the polypeptide chains of the antibody are expressed in a balanced manner.

The nucleotide sequence encoding at least the part of the murine IgG2a subtype amino acid sequence is preferably ligated into the nucleotide sequence encoding the kappa light chain or the gamma heavy chain by one of insertion or substitution techniques to obtain an antibody expression construct. The nucleotide sequence encoding the kappa chain and a nucleotide sequence encoding the gamma chain are preferably linked by an IRES sequence.

A vector according to the invention comprises a promotor, an antibody-expression construct as described above and a transcription termination sequence. The vector preferably contains one of the IRES sequences in the attenuated form. Through an inserted sequence the IRES sequence may be attenuated to downregulate the entry of the ribosomes and the expression of a quantitative selection marker operatively linked thereto. Thus, those host cells that produce the selection marker and the expression product at the highest level can easily be selected. The IRES sequence is preferably attenuated by insertion of the sequence to locate it pre and/or post the IRES sequence. The insertion sequence may encode a hairpin.

Insertion of overhangs/IRES flaning regions that significantly reduce efficiency of (cap-independent) initiation of translation might be of preference.

Among the preferable selection markers there is the DHFR (dihydrofolate reductase) gene, which is an essential component for the growth of transfected DHFR deficient CHO cells in the presence of MTX (methotrexate). Alternatively, also other selection and amplification markers can be used, such as hygromycin-B-phosphotransferase, thymidine kinase etc. Using an IRES sequence a selection marker will integrate exactly at the same site as the foreign gene and selection will occur on the same mRNA encoding for both antibody chains and also the selection marker. By attenuating this second IRES sequence, translation efficiency of the selection marker will strongly be reduced. The use of a DHFR deficient CHO strain enables selection and gene copy number amplification using low selective concentrations of MTX ranging from 1 to 10 µmol/l.

A bicistronic pIRES expression vector is commercially available (Clontech laboratories Inc, Palo Alto, USA). This construct can be modified to produce the heavy and light antibody chains at nearly the same high expression levels.

The preferred method of producing an antibody according to the invention comprises the steps of transforming a CHO host cell with a multicistronic antibody-expression construct containing at least a nucleotide sequence encoding a kappa light chain and a nucleotide sequence encoding a gamma heavy chain, wherein at least one of the nucleotide sequences comprises a nucleotide sequence encoding at least a part of a murine IgG2a subtype amino acid sequence, and at least two IRES elements, and expressing said nucleotide sequences of immunoglobulines under the control of a single CMV promoter to produce an intact antibody, transcription of a single RNA comprising protein sub-units and selection marker.

Employing the method according to the invention it has proven that the kappa light chain and gamma heavy chains are expressed in about equimolar quantity. The antibody concentration obtained proved to be at least 1 µg/ml, preferably 5-300 µg/ml.

The following examples are describing the invention in more detail, but not limiting the scope of the invention.

EXAMPLES

I. Production of Recombinant Mouse IgG2a mAb17-1A Antibody (r mAb17-1A,)

Example 1

Molecular Biological Constructs

The bicistronic pIRES expression vector (FIG. 1) purchased from Clontech laboratories Inc., Palo Alto, USA allows to express two genes at high level and enables the translation of two consecutive open reading frames from the same messenger RNA. In order to select positive transformants using a reporter protein, the internal ribosome entry site (IRES) in this expression vector has been truncated enabling lower expression rates of this second reading frame. Therefore, the original IRES sequence had to be re-established in order to satisfy our purposes expressing heavy and light antibody chain at nearly the same expression level. The attenuated IRES sequence is used for the expression of our selection marker.

DNA manipulations were done by standard procedures. Using PCR technology and the Advantage-HF PCR Kit (CLONTECH laboratories Inc., Palo Alto, USA), the heavy and the light chain of the mAb17-1A (HE-2) antibody were amplified using primers introducing the respective cleavage sites for restriction endonucleases necessary for the introduction of the gene into the expression vectors once and twice the Kozak-sequences upstream of the open reading frames. The autologous signal sequences were used to direct nascent polypeptide chains into the secretory pathway. Primers were purchased from MWG-Biotech AG, Germany. FIG. 2 shows the cloning cassette used for the bicistronic expression of mAb17-1A (HE-2). A two step cloning strategy was performed: Kappa-chain including its autologous signal sequence was amplified as Xho I, Mlu I fragment and ligated into the expression vector using the Rapid ligation kit (Roche, Germany) according to the instructions of the manufacturer. The construct was transfected into chemical competent E. coli bacterial strain DH5alpha, (Gibco BRL) and amplified using the ampicilline selection marker. In a second step, the reconstructed IRES sequence and Gamma chain, also including its autologous signal sequence, were amplified as Mlu I, Nco I and Nco I, Sal I fragments respectively and ligated in a single step ligation reaction into the modified expression vector already containing the mAb17-1A Kappa chain. This construct was amplified using the bacterial strain DH5alpha (Gibco BRL). Twenty-five constructs deriving from different PCR samples were digested using the restriction endonucleases EcoR I and BamH I. Constructs showing the correct digestion map were bi-directionally sequenced. In this expression construct, the selection cassette described below was introduced. The selection marker DHFR was amplified as PCR Xba I/Not I fragment from the pSV2-dhfr plasmid (ATCC #37146). PCR-primers introduced these restriction sites. The attenuated IRES at. sequence was amplified by PCR from pSV-IRES (Clontech #6028-1) as Sal I/Xba I fragment. In a single step ligation reaction, IRES at. and DHFR was ligated into the already described expression construct after being digested with the corresponding restriction endonucleases and a further dephosphorylation step. After a transfection into the bacterial strain DH5alpha (Gibco BRL), positive transformants were screened by PCR. The correct insertion of selection and expression cassettes was proven by minipreparation and further digestion-map shown in FIG. 2. The constructs were bi-directional sequenced and used in further transfections in eukaryotic cells.

Example 2

Transfection

The characterized eukaryotic strain, CHO (ATCC-CRL9096), was transfected with the expression vector prepared as described above. The DHFR selection marker was used to establish stable cell lines expressing rmAb17-1A. In a six-well tissue culture plate, the cell line was seeded at densities of 105 cells in 2 ml complete Iscove's modified Dulbecco's medium with 4 mM L-glutamine adjusted to contain 1.5 g/L sodium bicarbonate and supplemented with 0.1 mM hypoxanthine and 0.016 mM thymidine, 90%; fetal bovine serum, 10% (Gibco.BRL). Cells were grown until 50% confluency. Cells were transfected according to the instructions of the manufacturer in absence of serum with 2 µg DNA using Lipofectin☐ reagent (Gibco-BRL). Transfection was stopped by addition of complete medium after 6 or 24 hours.

Example 3

Selection of Positive Transformants and Cultivation

Complete medium was replaced by selective medium 24 or 48 hours post transfection. FCS in complete medium was replaced by dialyzed FCS (Gibco.BRL, origin: south America). 10 days post selection, positive transformands appeared as fast growing multicellular conglomerates. Concentration of rmAb17-1A was analyzed in supernatants by a specific sandwich ELISA recognizing both the variable and the constant domain of the antibody. Cells showing high productivity were splitted 1:10 and expanded into 75 cm2 cell culture flasks for preservation into liquid nitrogen. In parallel, these producers were exposed to an increasing selection pressure by adding Methotrexate to the culture medium and seeding the cells into a six-well cell culture plate. Procedure was repeated about two weeks later when cells reached stable growth kinetics. Starting from a concentration of 0.005 µM, MTX concentration was doubled each round of selection until finally a concentration of 1.280 µM MTX was reached and sub cultured in parallel into 96-well tissue culture plates. Supernatants were analyzed weekly by a specific sandwich ELISA recognizing both the variable and the constant domain of the antibody. Stable cultures showing highest productivity were transferred into 75-cm2 cell culture flasks and stepwise expanded finally into 860-cm2 rolling tissue culture flasks in non selective medium. Supernatants were harvested, centrifuged, analyzed and submitted to further purification.

Example 4

Production of rmAb17-1A Under Serum Free Conditions

Recombinant rmAb17-1A was produced in lab-scale by engineered CHO cell-line using protein free medium EXCELL® 325 PF (JRH Biosciences) in roller-bottles. The supernatants were affinity purified using the anti-idiotypic antibody IGN111 immobilized onto SEPHAROSE® and characterized by SDS-PAGE, SEC-HPLC, ELISA and IEF.

Example 5

Analysis of Expression Products

Supernatants were analyzed by specific ELISA recognizing both, the variable and the constant domain of the expressed antibody. The polyclonal anti-idiotypic antibody IGN111 was coated at 10 µg/ml onto MAXISORP™ (NUNC) sorption plates. This anti-idiotypic antibody was raised by immunization with mAb17-1A F(ab)2 fragments. The induced overall immune response was negatively affinity purified using immobilized 16B13ab, a murine IgG2a antibody of identical isotype but different specificity. Flow through fractions were affinity purified using immobilized mAb17-1A F(ab)2. Remaining antibodies against mouse constant regions were absorbed to a column on which polyclonal mouse IgG was immobilized. The final product, the polyclonal IGN111 antibody preparation thus recognizes the variable domain of mAb17-1A. Remaining active groups were blocked by incubation with 1% skim milk and supernatants were applied. Expressed antibodies were detected by their constant domains using a rabbit-anti-mouse-IgG2a-HRP conjugate (Biozym). Quantification was performed by comparison to an also loaded and characterized mAb17-1A standard hybridoma antibody.

Size determination of expressed proteins was performed by SDS-Polyacrylamide gel electrophoresis using 4-14% acryl amide gradient gels in a NOVEX™ (Gibco-BRL) electrophoresis chamber. Proteins were silver-stained. To detect the expressed antibodies immunologically, Western-blots were carried out on nitrocellulose membranes (0.2 µm). Proteins separated on SDS-Polyacrylamide gels were electro transferred using a NOVEX™ (Gibco-BRL) blotting-chamber. The membranes were washed twice before adding blocking solution (TBS+3% Skim Milk Powder BBL) and the antibody solution (10 µg/ml polyclonal goat IGN-111 antibody, mouse monoclonal anti-mouse IgG antibody (Zymed) or rabbit anti-mouse IgG gamma chain (Zymed) in TBS+1% Skim Milk Powder). Finally development was performed using a rabbit anti-goat-HRP, rabbit anti-mouse IgG-HRP or mouse anti-rabbit IgG-HRP conjugated antibody (BIO-RAD) diluted at 1:1000 in TBS+1% Skim Milk Powder and an HRP color development reagent (BIO-RAD) according to the manufacturers instructions.

Isoelectric focusing gels were used to compare the purified expression products to the characterized murine mAb17-1A standard hybridoma antibody. Samples were loaded onto IEF gels, pH 3-7 (Invitrogen) and separation was performed according to the instructions of the manufacturer. Proteins were visualized by silver stain or by immunological methods by Western-blot. For this purpose, proteins were charged in a Tris buffered SDS/Urea/Iodoactamide buffer and transferred onto nitrocellulose membranes using the same procedure described for Western-blots. Detection was performed using the polyclonal goat IGN111 anti-idiotypic antibody.

Interaction of expression products with their target antigen, EpCAM was analyzed by incubating purified supernatants with Nitro-cellulose membranes on which rEpCAM was electro-transferred. Staining of interacting antibodies was performed in analogy to Westen-blots using an anti-mouse IgG2a-HRP conjugated antibody (Zymed).

Example 6

Affinity Purification

A Pharmacia (Amersham Pharmacia Biotech) ÄKTA system has been used. 1000 ml clarified culture supernatant containing antibody were concentrated using a Pro-Varion 30 kDa cut-off (Millipore) concentrator, then diluted with PBS and loaded onto a 20 ml IGN111 SEPHAROSE® affinity gel XK26/20 column (Amersham Pharmacia Biotech). Contaminating proteins were discarded by a wash step with PBS+200 mM NaCl. Bound antibodies were eluted with 100 mM Glycine, pH 2.9 and neutralized immediately using 0.5 M $NaHCO_3$. Effluent was online monitored at $\Lambda$ 215 and $\Lambda$ 280 nm and submitted to a subsequent HPLC analysis using a ZORBAX® G-250 (Agilent-technologies) column.

2000 ml harvested supernatants, deriving from roller bottle cultures were centrifuged, concentrated, diluted in PBS and purified to homogeneity by affinity chromatography using the IGN111 SEPHAROSE® column. After elution, neutralization and dialysis against PBS, final product was measured by SEC-HPLC. A hybridoma derived murine standard of the same immunoglobulin was compared with rmAb17-1A and eluted, both as sharp single peaks, at the same time, correlating with the expected retention time of IgG. Purity >92% was reached using this laboratory scale purification strategy.

Further characterization of the expression product was carried out by reducing and non reducing silver stained SDS-PAGE and Western-Blot. The expression products were detected by the specific, anti-idiotypic antibody goat anti mAb17-1A, IGN111, and visualized by an anti-goat-HRP conjugated antibody. Not reduced samples showed bands in the expected range of an intact IgG molecule corresponding to 160 kDa. This result correlates exactly with the murine standard mAb17-1A hybridoma antibody. In the case of reduced samples, bands in the range of 25 and 50 kDa, also interacting with the anti-idiotypic goat anti mAb17-1A antibody IGN111, are visible. Those bands correspond to IgG light and heavy chains respectively.

Interaction with the target antigen of mAb17-1A, EpCAM was analyzed by incubating Nitro-cellulose membranes on which rEpCAM has been electro-blotted, with purified expression products. Further subtype specific detection of interacting antibodies was done. The murine mAb17-1A standard hybridoma antibody recognizes the monomeric rEpCAM of 25 kDa and also a series of rEpCAM aggregates, corresponding to di, tri, and polymeric forms. Exactly the same band distribution is found for all purified expression products.

Purified expression products and the murine mAb17-1A standard hybridoma antibody were further analyzed. All antibodies show an inhomogeneous polybanded isoelectric focusing-pattern, identical in pH but different in quantitative distribution, consisting in three major protein isoforms and two sub forms, distributed over a pH range of 8.2 to 7.2. CHO derived isoforms are shifted to higher pH values, the murine mAb17-1A standard shows the identical isoforms, but quantitative distribution tends towards acidic forms.

We were able to express recombinant mouse IgG2a antibody mAb 17-1A in CHO cells. Stable genomic integration occurred 14 days after transfection. The expression construct enabled rapid and comfortable transfection using a single plasmid. By the use of a selection system based on an essential metabolic enzyme depleted host strain, a plasmid carrying the corresponding gene ant a potent antagonist of this enzyme, gene copy number could be increased by continuous increasing selection pressure. The use of an attenuated IRES sequence in the expression cassette of this selectable marker, very low amounts of the antagonist MTX could be used for the selection strategy. Moderate expression was achieved with levels about 10 μg/24 h.ml, which could be kept at least 5 weeks in production cultures. Purified expression products did not differ from the murine mAb 17-1A standard in size and specific immunological essays. Nevertheless, differences in post translatorial modifications may have occurred. Therefore, recombinant antibodies showed a host or medium specific isoelectric focusing pattern. Biological equivalence of the expression product are further analyzed in immunization studies.

Example 7

Rhesus Monkey Immunization Study

Study Protocol

A Rhesus monkey immunization study was performed at BioTest s.r.o. facilities (Conarovice, CZ). Immunogenicity of IGN101 (mAb17-1A) and IGN101 (recombinant-mAb17-1A) was compared in naïve Rhesus monkeys. Each treatment group consisted of 2 male and 2 female monkeys (4-6 kg body weight). A single dose of 0.5 mg of the respective mAb17-1A formulated onto $Al(OH)_3$ was administered subcutaneously on days 1, 15, 29 and 57. Serum samples were taken from monkeys 11 days before first vaccination and on study days 1, 15, 29, 57, and 71. Serum samples were taken before each vaccination. All serum samples taken before immunization (i.e. day-11 and day 1) are considered as pre-immune sera (Pre-IS).

Immunogenicity was assessed as a primary objective of this study:
 Humoral immune response to the mAb17-1A antigen was examined by ELISA and by immunization antigen specific affinity chromatography.
Preparation of Study Medication
 As mentioned above 2 types of drug substance (mAb17-1A) were used this study: hybridoma-derived mAb17-1A and recombinant mAb17-1A (lab scale). All types were adsorbed onto $Al(OH)_3$ in the same amounts and concentrations.
Recombinant mAb17-1A
 r-mAb17-1A was produced in lab-scale by the engineered CHO cell-line (E5 WCB 325 R11/1a) in roller-bottles using protein-free medium EXCELL® 325 PF (JRH Biosciences). The supernatant was affinity purified using Protein A SEPHAROSE®. Purified recombinant mAb17-1A was characterized by SDS-PAGE, SEC-HPLC, ELISA and IEF.
Analysis of Immune Response
 Immunization antigen-specific (mAb17-1A) ELISA
Method Description
 Pre-immune sera and immune sera of different time points were analyzed by an immunization antigen-specific ELISA recognizing induced humoral immune response. This was performed using mAb17-1A as coating antibody coated at 10

μg/ml onto MAXISORP™ (NUNC) sorption plates diluted in coating buffer (PAA). Remaining active groups were blocked by incubation with 3% FCS (Gibco BRL, heat inactivated) in PBS before sera were applied in 6×1:3 dilutions in PBS supplemented with 2% FCS. Induced antibodies were detected by their constant domains using a rabbit-anti-human-IgG, A, M-HRP conjugate (Zymed). Staining was performed by OPD (Sigma) in staining buffer (PAA) using H2O2 as substrate according to the manufacturer's instructions. Absorbance at 492 nm was measured using 620 nm as reference wavelength. Quantification was performed by comparison with a loaded and characterized Rhesus monkey immune serum of a previous immunization study (8415F day 94), which is standardized equivalent to a titer of 1:9000.

Results and Discussion

Substantial titers of antibodies against mAb17-1A were induced in all 2 treatment groups: Antibody titers against mAb17-1A appeared on day 15, remaining at a high level between day 29 and day 71 (Table 1). There was no significant difference in kinetics and extent of the immune response induced either by IGN101 (mAb17-1A) or IGN101 (r-mAb17-1A).

TABLE 1

Immunization antigen (mAb17-1A)-specific titer (ELISA)

| Treatment group/ animal number | Day of treatment: | | | | | |
|---|---|---|---|---|---|---|
| | 0 | 8 | 15 | 29 | 57 | 71 |
| mAb17-1A | | | | | | |
| 128 | 1* | 1 | 653 | 1561 | 1844 | 7940 |
| 150 | 1 | 1 | 1300 | 30693 | 16976 | 20106 |
| 109 | 1 | 1 | 8040 | 33000 | 27160 | 49885 |
| 289 | 1 | 1 | 11255 | 23435 | 18863 | 36197 |
| Geometric mean | 1 | 1 | 2960 | 13874 | 11253 | 23171 |
| CI+ | 1 | 1 | 20204 | 105838 | 61407 | 71032 |
| CI− | 1 | 1 | 434 | 1819 | 2062 | 7559 |
| r-mAb17-1A | | | | | | |
| 140 | 1 | 1 | 1156 | 6296 | 4151 | 15072 |
| 265 | 1 | 1 | 8948 | 18189 | 19776 | 45544 |
| 184 | 1 | 1 | 8221 | 24846 | 5672 | 26012 |
| 121 | 1 | 1 | 37 | 369 | 3894 | 23367 |
| Geometric mean | 1 | 1 | 1332 | 5692 | 6525 | 25415 |
| CI+ | 1 | 1 | 47115 | 81371 | 18666 | 47789 |
| CI− | 1 | 1 | 38 | 398 | 2281 | 13516 |

*values below detection limit were replaced by '1' for statistical evaluations

Affinity Chromatography

Rationale and Method Description

The amount of IgG and IgM of total antibodies induced against the respective immunization antigen (mAb17-1A or r-mAb17-1A) were quantified as follows: In a first step the respective immunization antigen was coupled to CH-SEPHAROSE® 4B (2 mg/ml) and filled into a 1 ml chromatography column. 1.0 ml of monkey serum (pre-immune (day-11) and immune sera from day 29, 57 and 71) was diluted 1:10 in running buffer (PBS supplemented with 200 mM NaCl) and loaded onto the column. The unbound sample was washed out with running buffer. Fractions of interest containing the antigen-specific humoral immune response were desorbed with elution buffer (100 mM Glycine/HCl, pH=2.9) and collected by automated fractionation and immediately neutralized by adding 1.0 M NaHCO3.

Total immunoglobulin concentration and IgG and IgM ratio in eluted fractions were determined by size exclusion chromatography using a ZORBAX® GF 250 column. Commercially available, polyclonal human IgG and IgM (PENTAGLOBIN®) was used as standard.

Results and Discussion

Induced Immunization Antigen Specificity

All two treatment groups raised a strong immunization antigen-specific IgG immune response (Table 2). IgG increased in all groups from day 29 to 71. Levels of immunization antigen-specific immune titres were found to be very similar in groups vaccinated with either IGN101 (mAb17-1A) or IGN101 (r-mAb17-1A). Due to small group size and interindividual variability no significant differences could be determined.

TABLE 2

Induced immunization antigen-specific IgG
(μg IgG/ml; affinity chromatography)

| Treatment group/ animal number | Day of treatmen | | | |
|---|---|---|---|---|
| | −11 | 29 | 57 | 71 |
| mAb17-1A | | | | |
| 128 | 13.2 | 15.4 | 59 | 126.9 |
| 150 | b.d. | 128.4 | 232.6 | 257.4 |
| 109 | b.d. | 232.2 | 203.9 | 436.5 |
| 289 | b.d. | 97.6 | 122.1 | 184.4 |
| Average | 3.3* | 118.4 | 154.4 | 251.3 |
| standard deviation | 6.6 | 89.6 | 79.0 | 134.5 |
| CI | 9.2 | 124.4 | 109.6 | 186.7 |
| r-mAb17-1A | | | | |
| 140 | b.d. | 20 | 102.11 | 202.105 |
| 265 | b.d. | 116.7 | 104.73 | 217.4 |
| 184 | b.d. | 93.8 | 225.88 | 283.6 |
| 121 | b.d. | 55.2 | 97.12 | 243.7 |
| Average | | 71.4 | 132.5 | 236.7 |
| standard deviation | | 42.7 | 62.4 | 35.7 |
| CI | | 59.2 | 86.6 | 49.5 | n.a. not analyzed
b.d. below detection limit (i.e. 12.0 μg/ml)
*for statistic calculations values below detection limit were set '0'

TABLE 3

Induced immunization antigen-specific IgM
(μg IgM/ml; affinity chromatography)

| Treatment group/animal number | Day of treatment: | | | |
|---|---|---|---|---|
| | −11 | 29 | 57 | 71 |
| mAb17-1A | | | | |
| 128 | 31.8 | 34.8 | 19.6 | 28.9 |
| 150 | b.d. | 19.5 | 22 | 20.1 |
| 109 | b.d. | 16.7 | 20.3 | 24 |
| 289 | b.d. | 13.1 | 13.8 | 14.3 |
| Average | 8* | 21.0 | 18.9 | 21.8 |
| standard deviation | 15.9 | 9.5 | 3.6 | 6.2 |
| CI | 22.1 | 13.3 | 4.9 | 8.6 |
| r-mAb17-1A | | | | |
| 140 | b.d. | 6.9 | 9.5 | 19.65 |
| 265 | 6.8 | 9.3 | 19.4 | 23.9 |
| 184 | 6.3 | 7.1 | 18.6 | 22.15 |
| 121 | 30.1 | 73.5 | 40.8 | 37.38 |
| Average | 14.4 | 24.2 | 22.1 | 25.8 |
| standard deviation | 13.2 | 32.9 | 13.3 | 7.9 |
| CI | 18.4 | 45.6 | 18.4 | 11.0 | n.a. not analyzed
b.d. below detection limit (i.e. 3.5 μg/ml)
*for statistic calculations values below detection limit were set '0'

'Cross Comparative' ELISA
Rationale and Method Description

This assay was carried out with immune-sera (day 71) of Rhesus monkeys vaccinated with either IGN101 (mAb17-1A) or IGN101 (r-mAb17-1A). The aim of the 'cross comparative ELISA' is to directly compare e.g. epitope specificity of the respective immune responses of the two vaccine antigens:

1) Antibodies induced by IGN101 (mAb17-1A) immunization are applied to ELISA plates coated with mAb17-1A or r-mAb17-1A.

2) Binding activity of antibodies induced by IGN101 (rmA17-1A) immunization are tested on ELISA plates coated with mAb17-1A or r-mAb17-1A.

Results and Discussion

FIG. 10 shows the results of the experiment. Cross-comparative ELISA analysis. Geometric means (4 animals per group) and CI (95%) are shown.

No difference in humoral immune response was found comparing immune sera induced by vaccination with either IGN101 (mAb17-1A) or IGN101 (r-mAb17-1A) regarding mAb17-1A or r-mAb17-1A binding specificity. Single values of each Rhesus monkey are given in Annex 1. Results suggest that exactly the same immunogenic epitopes are presented in both types of vaccines.

Repeated Dose Safety Pharmacology and Toxicity Study

A 13-week safety pharmacology study has started in November 2003 at Covance Laboratories GmbH (Munster, Germany). This study is conducted in compliance with the Good Laboratory Practice Regulations. As for previous animal studies, Rhesus monkeys (Macacca mulatta) are used for toxicity testing.

Dose, vaccination schedule, and administration of the test substance reflect the intended clinical use as well as previous animal studies and numerous clinical trials performed with IGN101 (mAb17-1A):

Primary vaccination are being performed on days 1, 15, and 29. On day 57 a booster injection is given. All injections are administered subcutaneously in a volume of 0.5 ml per single dose. As in a previous study, the total observation period was set to 93 days. Dose selection is based on considerations outlined in the description of the previous animal study: 500 µg mAb17-1A (~90 µg/kg), adsorbed on aluminum hydroxide per single dose. One treatment group is immunized with IGN101 (mAb17-1A), a second receives IGN101 (r-mAb17-1A). The recombinant antibody stems from a GMP batch. The placebo group is treated with the equivalent formulation lacking the antibody compound.

Each treatment group consists of 2 male and 2 female Rhesus monkeys (n=4).

Clinical and physiological examinations are being performed in all animals. Food intake, general behavior and body weight are recorded at regular intervals. Haematological, immunological parameter, urinalysis and parameter of clinical chemistry are determined at relevant intervals (bleeding schedule, outlined below).

Terminal Monitoring

Autopsy will be conducted on all animals. Organ weights, macroscopic and histopathological observations are recorded for all commonly examined tissues. Tissue samples are conserved for further examinations.

Pharmacodynamics

Immunological analyses are included into repeated dose toxicity and take into account the pharmacodynamic and -kinetic profiles as obtained from the previous animal study, clinical trials and results published from related studies (Galili, U. (1993) Interaction of the natural anti-Gal antibody with alpha-galactosyl epitopes: a major obstacle for xenotransplantation in humans. Immunology Today; 14(10): 480-2, Frodin, J. E., Lefvert, A. K. & Mellstedt, H. (1990). Pharmacokinetics of the mouse monoclonal antibody 17-1A in cancer patients receiving various treatment schedules. Cancer Res 50, 4866-71.). Specific ELISAs as well as chromatographic approaches are performed to quantify and characterize the immunological response in blood samples:

a) Total immune response is shown by an ELISA specific for the immunization antigen (mAb17-1A). A subclass ELISA is performed to characterize the type of immune response. A 'cross comparative ELISA' is performed to examine immune sera from animals vaccinated with recombinant mAb17-1A by comparing their binding properties to the immunization antigen (i.e. r-mAb17-1A) as well as to the hybridoma-derived mAb17-1A. This is done vice versa with sera of animals vaccinated with the hybridoma mAb17-1A. It is anticipated that the immune sera display similar binding properties irrespective of the antibody coated to the ELISA plates.

b) Target antigen-specific antibody reactions will be demonstrated with a sequential affinity chromatography.

In addition to final observations these parameters are monitored with a frequency that permits an assessment of changes over time: Blood samples for immunological analysis and kinetics are taken once before the start of study (day-14), on day 1 (directly prior to vaccination, 1, 4 and 24 hours after vaccination) and on days 43, 71 and 92 in the morning and at necropsy during exsanguination (day 93).

Specific studies for $Al(OH)_3$ are not being performed, since the profile of the commonly used adjuvant has been examined and well documented (Weiner, L. M. et al. (1993). Phase II multicenter evaluation of prolonged murine monoclonal antibody 17-1A therapy in pancreatic carcinoma. J Immunother 13, 110-6)

The metabolic pathway of antibodies is well understood, thus obviating the need of biotransformation studies.

Local Tolerance

Testing for local tolerance is included within repeated dose toxicity study.

Preliminary Results

The first of four subcutaneous vaccinations of IGN101 was well tolerated and did not reveal any adverse toxic signs: There were no clinical signs that could be ascribed to treatment with the test article. No skin changes at the injection sites were observed and no signs of abnormal local tolerance were reported.

Summary and Conclusion

First results of serum sample analyses of monkeys vaccinated with either IGN101 (mAb17-1A) and IGN101 (r-mAb17-1A) show that both types of antigens induce a comparable immune response in Rhesus monkeys. Moreover, the extent of induced immune response was found to be essentially similar in both groups.

Side-by-side biochemical characterization of both vaccine antigens has shown that the two antigens are very similar in protein structure and binding activity. In addition, it was shown that the immune response elicited by both vaccine antigens was found to be essentially similar in quality and quantity as analyzed so far. Igeneon will pursue the characterization of the immune response induced in Rhesus monkeys but also in patients to verify the hypothesis that the immune response induced by either vaccine antigen will be essentially similar.

TABLE 4

Induced immunization antigen-specific titres
('Cross comparative' ELISA)

| Treatment group/animal number | Coated with r-mAb17-1A | Coated with mAb17-1A |
|---|---|---|
| mAb17-1A | | |
| 128 | 6520 | 8326 |
| 150 | 25371 | 24733 |
| 109 | 21559 | 22682 |
| 289 | 13486 | 19621 |
| geomean | 14809 | 17399 |
| CI+ | 34485 | 34855 |
| CI− | 6359 | 8685 |
| r-mAb17-1A | | |
| 140 | 12789 | 12822 |
| 265 | 12946 | 12237 |
| 184 | 22009 | 20350 |
| 121 | 16172 | 16489 |
| geomean | 15581 | 15148 |
| CI+ | 22176 | 21031 |
| CI− | 10947 | 10910 |

Results

Considering all vaccinations, no side effects were observed. In this immunization study, the vaccination with different IgG2a formulations induced in all cases a strong IgG type immunization antigen specific immune response. Except for the deglycosylated 17-1A formulation which caused a lower immune response, the immunogenicity of all other formulations was nearly the same. Immune titers increased from values below the detection limit up to 300 µg/ml serum corresponding to an induced IgG ratio of nearly 1%. Immunogenicity of all applied glycosylated IgG2a antibodies was nearly in the same range, independent from their specificity.

Also independent from the immunization group, all IgG2a vaccinated animals raised an IgG type immune response recognizing EpCAM corresponding to an amount of 30-40% of the immunization antigen specific titer. Vaccination with IgG2a antibodies caused therefore a cross reactivity of the immune sera with EpCAM. Deglycosylation of the immunization antigen decreased both induced IgG levels significantly, the ones directed against the immunization antigen and the ones against EpCAM.

Deglycosylation considerably changes the immunogenetic properties of the antibody. Both the immunoglobulin titers against the immunization antigen and the target antigen were reduced.

The comparison between the original, hybridoma derived immunization antigen 17-1A and the recombinantly expressed r mAb 17-1A from CHO cells did not reveal any immunological differences. Both formulations showed identical kinetics building up the immunization antigen and target antigen specific immune response. Raised IgG and IgM titers were similar.

Example 8

Expression of a Hybrid Immunogenic Antibody

The recombinant IgG2a Le-Y antibody is an IgG2a hybrid antibody designed for primate vaccination. It combines an anti-idiotypic Lewis-Y (Le-Y) mimicking hypervariable region and the highly immunogenic mouse IgG2a constant regions.

A figure of the IgG2a Le-Y antibody is shown in FIG. 4. The recombinant IgG2a Le-Y antibody immunotherapy enhances the immunogenicity of the parent antibody IGN301 produced by a hybridoma cell. It induces a strong IgG type immune response directed against Le-Y and/or EpCAM overexpressed and presented on epithelial cancer cells. This immune response lyses tumor cells by complement activation or cell mediation preventing the formation of metastases.

Molecular biological constructs of the recombinant IgG2a Le-Y antibody were incorporated into the poly-cistronic expression vector described above as shown in FIGS. 1 and 2.

The recombinant IgG2a Le-Y antibody was expressed transiently in HEK293 cells calcium phosphate co-precipitation in a MicroSpin system in presence of FCS. After purification using an anti-Le-Y affinity column and qualification of the expression product, the recombinant IgG2a Le-Y antibody was formulated onto Al(OH)$_3$ and administered as vaccine in a Rhesus monkey immunization study using four 500 µg doses.

High immunogenicity in comparison with the parent vaccine IGN301 could be observed. The induced IgG type immune response was analysed by ELISA and showed an immunisation antigen, Le-Y specificity.

---

The invention claimed is:

1. An immunogenic recombinant antibody fragment comprising a protein sequence secreted from a cell comprising an expression vector including a DNA encoding either SEQ ID NO: 3 or SEQ ID NO: 4, and at least a part of the murine IgG2a subtype amino acid sequence, wherein the protein has hamster or primate glycosylation.

2. An immunogenic recombinant antibody or antibody fragment comprising a protein sequence secreted from a cell comprising an expression vector including a DNA encoding at least one of SEQ ID NO: 2, 3, 4, or 5 and at least a part of the murine IgG2a subtype amino acid sequence.

3. The immunogenic recombinant antibody or antibody fragment of claim 2, further comprising hamster or primate glycosylation.

4. The immunogenic recombinant antibody or antibody fragment of claim 3, further comprising hamster glycosylation and which is produced in CHO cells.

5. An immunogenic recombinant antibody or antibody fragment comprising a protein sequence secreted from a cell comprising an expression vector including a DNA encoding SEQ ID NO: 2 and at least one of SEQ ID NOs: 3, 4, or 5, and at least a part of the murine IgG2a subtype amino acid sequence.

6. The antibody or antibody fragment of claim 1 or 2 wherein said antibody comprises the murine IgG2a subtype amino acid sequence.

* * * * *